US011963724B1

(12) United States Patent
Roh et al.

(10) Patent No.: US 11,963,724 B1
(45) Date of Patent: Apr. 23, 2024

(54) SYSTEMS AND METHODS FOR DESIGNING AND SIMULATING 3D PRINTED IMPLANTS

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael John Baker, Georgia, VT (US)

(73) Assignee: 1X Innovation LLC, Seattle, WA (US)

( * ) Notice: Subject to any disclaimer, the term of this patent is extended or adjusted under 35 U.S.C. 154(b) by 0 days.

(21) Appl. No.: 18/216,209

(22) Filed: Jun. 29, 2023

(51) Int. Cl.
G06K 9/00 (2022.01)
A61B 34/10 (2016.01)
A61K 35/12 (2015.01)
G06T 7/00 (2017.01)
G16H 10/60 (2018.01)
G16H 30/20 (2018.01)
G16H 50/50 (2018.01)

(52) U.S. Cl.
CPC ............ A61B 34/10 (2016.02); G06T 7/0012 (2013.01); G16H 10/60 (2018.01); G16H 30/20 (2018.01); G16H 50/50 (2018.01); *A61B 2034/102* (2016.02); *A61B 2034/105* (2016.02); *G06T 2200/08* (2013.01)

(58) Field of Classification Search
CPC .......... G06K 9/00; A61B 34/25; A61B 34/10; A61K 35/12

USPC ........ 382/100, 103, 106–107, 128, 131–132, 382/154, 156, 172, 173, 181, 189, 199, 382/209, 219, 254, 274, 285–291, 305, 382/321; 623/908, 23.63, 1.49
See application file for complete search history.

(56) References Cited

U.S. PATENT DOCUMENTS

| 9,250,620 B2 * | 2/2016 | Kotlus ................. A61F 2/0059 |
| 2005/0148843 A1 * | 7/2005 | Roose .................... A61B 17/17 623/908 |
| 2007/0233272 A1 * | 10/2007 | Boyce ................. A61L 27/3691 623/23.63 |
| 2022/0409140 A1 * | 12/2022 | Cordonnier ........... A61B 34/25 |
| 2023/0000560 A1 * | 1/2023 | Roh ...................... G06T 19/006 |

* cited by examiner

*Primary Examiner* — Seyed H Azarian
(74) *Attorney, Agent, or Firm* — Fish & Richardson P.C.

(57) ABSTRACT

This specification describes systems, methods, devices, and related techniques for optimizing 3D printed implants. A 3D network can collect medical images from an imaging device and create a 3D image of the damaged or malfunctioning body part. The 3D network allows a user to alter the 3D image to fix the damages or malfunctions and the 3D network, compares the altered 3D image to a historical database containing healthy patient's medical images, and provides recommendations to allow the user to further enhance the altered 3D image. The 3D network then performs a simulation on the enhanced 3D image to determine, if the 3D image was printed, if it will be successful or not. Once successful, the 3D image is printed using a 3D printer and the user tests the compatibility of the 3D printed object to determine if the implant or transplant would be successful.

17 Claims, 11 Drawing Sheets

Patient Image Data 900

| Patient ID | Region | MRI | CT Scan | X-Ray | Ultrasound | PET | 3D image | Altered 3D Image | Enhanced 3D image |
|---|---|---|---|---|---|---|---|---|---|
| IS123 | Chest | IS123MRI.data | - | - | - | - | | | |
| IS123 | Chest | - | IS123CT.data | - | - | - | | | |
| IS123 | Chest | - | - | IS123Xray.data | - | - | IS123-3D.data | IS123-Altered3D.data | IS123-Enhanced3D.data |
| IS123 | Chest | - | - | - | IS123US.data | - | | | |
| IS123 | Chest | - | - | - | - | IS123PET.data | | | |
| , | , | , | , | , | , | , | | | |
| , | , | , | , | , | , | , | | | |

FIG. 9

Historic Patient Data 1000

| Patient ID | Region | MRI | CT Scan | X-Ray | Ultrasound | PET |
|---|---|---|---|---|---|---|
| TB789 | Chest | TB789MRI.data | TB789CT.data | TB789Xray.data | TB789US.data | TB789PET.data |
| GT456 | Chest | GT456MRI.data | GT456CT.data | GT456Xray.data | GT456US.data | GT456PET.data |
| UP753 | Chest | UP753MRI.data | UP753CT.data | UP753Xray.data | UP753US.data | UP753PET.data |
| EL258 | Chest | EL258MRI.data | EL258CT.data | EL258Xray.data | EL258US.data | EL258PET.data |
| , | , | , | , | , | , | , |
| , | , | , | , | , | , | , |

FIG. 10

SYSTEMS AND METHODS FOR DESIGNING AND SIMULATING 3D PRINTED IMPLANTS

FIELD OF THE DISCLOSURE

The present disclosure is generally related to medical implants, particularly 3D printing, simulating, and optimization of customized medical implants inside, adjacent, affixed to, or otherwise around one or more anatomical structures of a patient's body.

BACKGROUND

Some patients may require procedures in which medical implants are custom-designed for a patient and inserted inside the patient's body. A procedure can be performed in which a surgeon or other medical practitioner designs an implant for part of the patient's body that has been damaged, and then inserts the implant inside the patient's body to provide therapeutic and/or diagnostic benefits before, during, and/or after the procedure. The surgeon can design then manually insert the implant inside the patient. The surgeon can also use robotic systems to assist in designing as well as accurately and safely inserting the implant inside the patient.

SUMMARY

The document generally relates to techniques for designing and optimizing implants for 3D printing inside a patient's body. Using the disclosed 3D bioprinting techniques, physicians, surgeons, or other medical professionals can customize a part of the patient's body that has been damaged. Similarly, these medical professionals can leverage computer-aided design (CAD) technology to use the damaged part of the patient's body as a starting point to then create alterations to a 3D printed implant design that may improve the damaged body part. Medical professionals also may leverage historic patient data of healthy patients into the design of the patient's 3D printed implant to improve or otherwise enhance functionality or performance of the 3D printed implant for the particular patient.

One or more embodiments described herein include a method for designing 3D printed objects for insertion into a body of a patient. The method includes receiving, from a medical imaging device, image data of at least a portion of a patient's body; generating, based on the image data, a 3D representation of the portion of the patient's body; retrieving, from a database, historic patient data for other patients that have a same or similar health condition as the patient; generating at least one recommendation for a design of a 3D printed object to be inserted into the portion of the patient's body based on a comparison of the 3D representation of the portion of the patient's body to the retrieved historic patient data; transmitting instructions to a user computing device that, when executed, cause the user computing device to output in a graphical user interface (GUI) display the 3D printed object and the at least one recommendation; receiving, from the user computing device, an altered 3D representation of the portion of the patient's body, where a user at the user computing device provided user input to alter the 3D representation based on the at least one recommendation; running a simulation to test the design of the 3D printed object based on the altered 3D representation of the portion of the patient's body; and returning simulation results based on running the simulation.

In some implementations, the embodiments described herein can optionally include one or more of the following features. For example, returning the simulation results can include: in response to a successful simulation result, executing instructions that cause a printing device to print the design of the 3D printed object according to the altered 3D representation. The printing device can be a 3D printer. The method can include: in response to printing the design of the 3D printed object, running another simulation to test compatibility of the printed object and a physiology of the patient. The method can include: in response to a successful simulation result from testing the compatibility of the printed object and the physiology of the patient, transmitting a notification to the user computing device indicating that the printed object is compatible with the physiology of the patient and is ready to be inserted into the patient's body. Returning the simulation results can include: in response to an unsuccessful simulation result, generating one or more other recommendations to modify the design of the 3D printed object. The method can include: iteratively modifying the design of the 3D printed object based on (i) user input indicating one or more modifications to the design of the 3D printed object based on the other recommendations and (ii) running one or more other simulations to test the modified design of the 3D printed object. The 3D representation of the portion of the patient's body can include an area of concern in the patient's body where the 3D printed object is to be inserted. The 3D printed object can be at least one of an implant, a stent, an apparatus, an anatomical structure, or an organ. Generating the at least one recommendation for the design of the 3D printed object to be inserted into the portion of the patient's body can include: scoring a result from the comparison of the 3D representation of the portion of the patient's body to the retrieved historic patient data, where a score value for the result is determined based on whether a size of the 3D printed object would fit within spatial limits of the portion of the patient's body. Running the simulation can include determining a success rate of printing the 3D printed object according to the design. Running the simulation can include determining a success rate of inserting the 3D printed object into the portion of the patient's body. Running the simulation can include determining whether the 3D printed object would interact with anatomical structures inside the patient's body near the portion of the patient's body where the 3D printed object is inserted. Running the simulation can include determining whether measurements of the 3D printed object are within a threshold range of measurements of an object in the portion of the patient's body that is to be replaced by the 3D printed object. Running the simulation can include determining a likelihood that the 3D printed object, once inserted into the portion of the patient's body, would fail or cause future health conditions for the patient. The method where the score value is assigned above a threshold score value based on a determination that the size of the 3D printed object is within a threshold size range as the portion of the patient's body. Implementations of the described techniques can include hardware, a method or process, or computer software on a computer-accessible medium.

One or more embodiments described herein include a system for designing 3D printed objects for insertion into a body of a patient. The system includes at least one imaging device configured to capture image data of at least a portion of a patient's body; a user computing device having a graphical user interface (GUI) display, where the user computing device is configured to receive and output information for designing an object to be 3D printed and inserted into the portion of the patient's body; a printing device configured to print the object; and a computing system in communication with the at least one imaging device, the user computing device, and the printing device, where the computing system is configured to perform operations can include: receiving, from the at least one imaging device, image data of at least a portion of the patient's body; generating, based on the image data, a 3D representation of the portion of the patient's body; retrieving, from a database, historic patient data for other patients that have a same or similar health condition as the patient; generating at least one recommendation for a design of a 3D printed object to be inserted into the portion of the patient's body based on a comparison of the 3D representation of the portion of the patient's body to the retrieved historic patient data; transmitting instructions to the user computing device that, when executed, cause the user computing device to output in a graphical user interface (GUI) display the 3D printed object and the at least one recommendation; receiving, from the user computing device, an altered 3D representation of the portion of the patient's body, where a user at the user computing device provided user input to alter the 3D representation based on the at least one recommendation; running a simulation to test the design of the 3D printed object based on the altered 3D representation of the portion of the patient's body; and returning simulation results based on running the simulation.

In some implementations, the embodiments described herein can optionally include one or more of the following features. For example, the system where the computing system can include: an imaging module configured to control operation of the at least one imaging device and generate the 3D representation of the portion of the patient's body; a design module configured to receive, from the user computing device, the altered 3D representation of the portion of the patient's body; an enhancement module configured to generate the at least one recommendation for the design of the 3D printed object; a simulation module configured to run the simulation module; and a print module configured to control operation of the printing device. Implementations of the described techniques can include hardware, a method or process, or computer software on a computer-accessible medium.

The devices, system, and techniques described herein can provide one or more of the following advantages. For example, the disclosed technology can facilitate minimally invasive procedures that reduce the incision size during the procedure and result reduced patient trauma and expedited patient recovery. The disclosed technology can facilitate the production and use of customized implants that can be precisely tailored to fit the patient's unique anatomy, improving fit and functionality. The disclosed technology can facilitate customizable adjustments to the implants to aid relevant users, such as doctors or medical professionals achieving an improved fit and functionality of the implants. The disclosed technology can improve patient outcomes and facilitate reduced instances of infection, reduces waste material, improved integration with surrounding tissues, and reduced manufacturing costs. The disclosed technology can facilitate expanded treatment options where relevant users, such as doctors or medical professionals can create complex, patient-specific implants that may not be feasible using traditional manufacturing methods.

Moreover, the disclosed technology provides CAD technology to aid relevant users, such as doctors or medical professionals, to create, modify, analyze, and/or optimize a design process for 3D printed objects, such as tissues and vessels for a patient. This technology can be used to increase productivity of the user, improve quality of design of the 3D printed objects, improve communications through documentation, and provide an organized way of storing and accessing data, patient information, and design information before, during, and/or after a surgical procedure involving the 3D printed object.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

DESCRIPTIONS OF THE DRAWINGS

FIG. 9 illustrates example image data that can be used to design and optimize a 3D printed implant.

FIG. 10 illustrates example historic patient data that can be used to design and optimize a 3D printed implant.

Like reference symbols in the various drawings indicate like elements.

DETAILED DESCRIPTION

This document generally relates to technology for designing objects to be 3D printed and inserted into a patient. The objects can include, for example, implants, organs, or other apparatus that can be printed using 3D printing techniques. The objects can be designed and printed to fit into a particular patient's body, specific to fit into an area of concern in the patient's body. Such objects can provide therapeutic and other health benefits to the patient. The disclosed technology can provide techniques for generating recommendations for improving the design of such objects and providing interactive graphical user interfaces (GUIs) to a computing device of a relevant user, such as a medical professional or doctor. The user can alter and/or enhance the design of such objects using the GUIs. The disclosed technology can provide for simulating and/or testing the altered and/or enhanced object design before 3D printing the object to then be inserted into the patient.

Figure 1A:
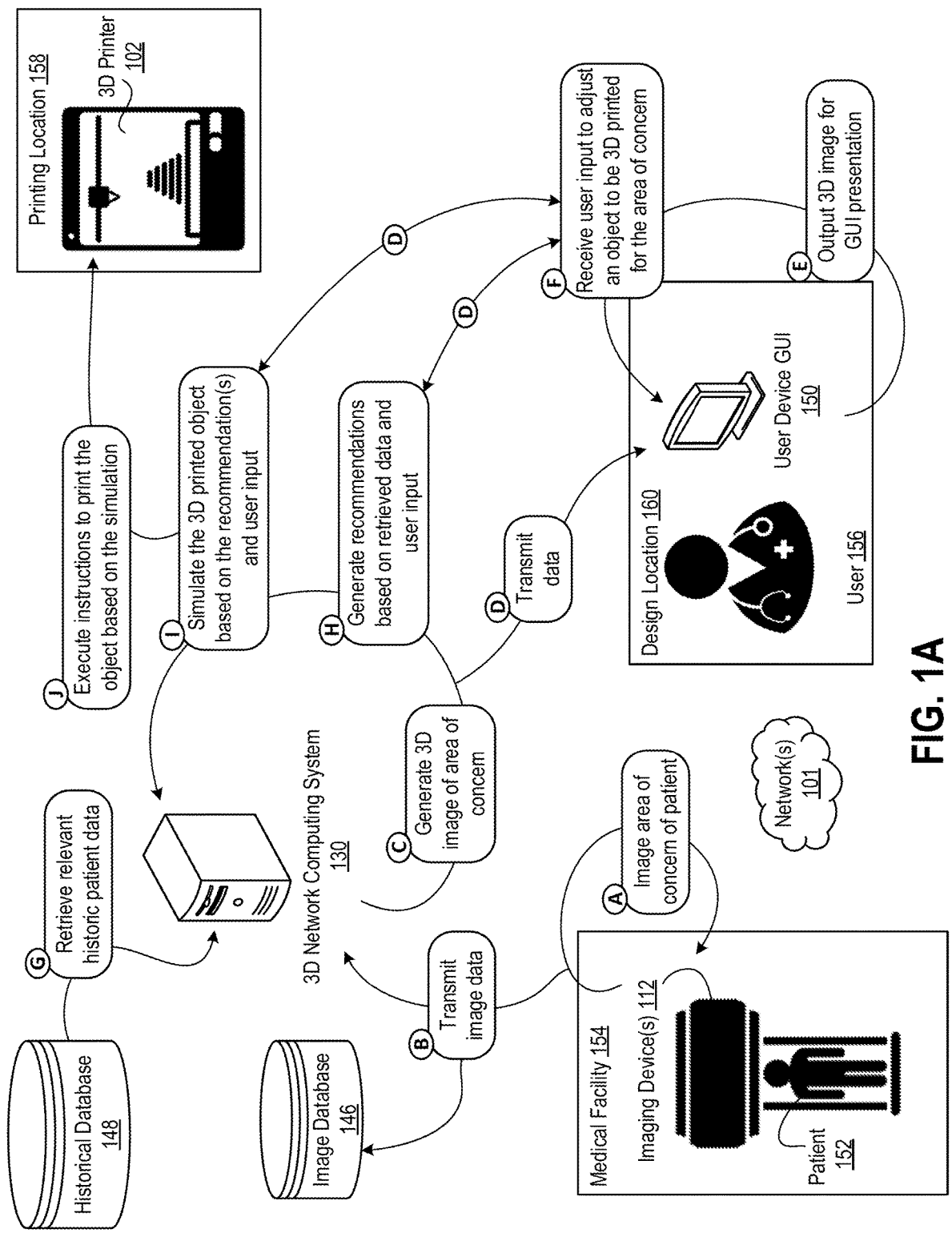
FIG. 1A is a conceptual diagram for designing and optimizing a 3D printed object to be inserted into an area of concern of a patient.
Figure 1B:
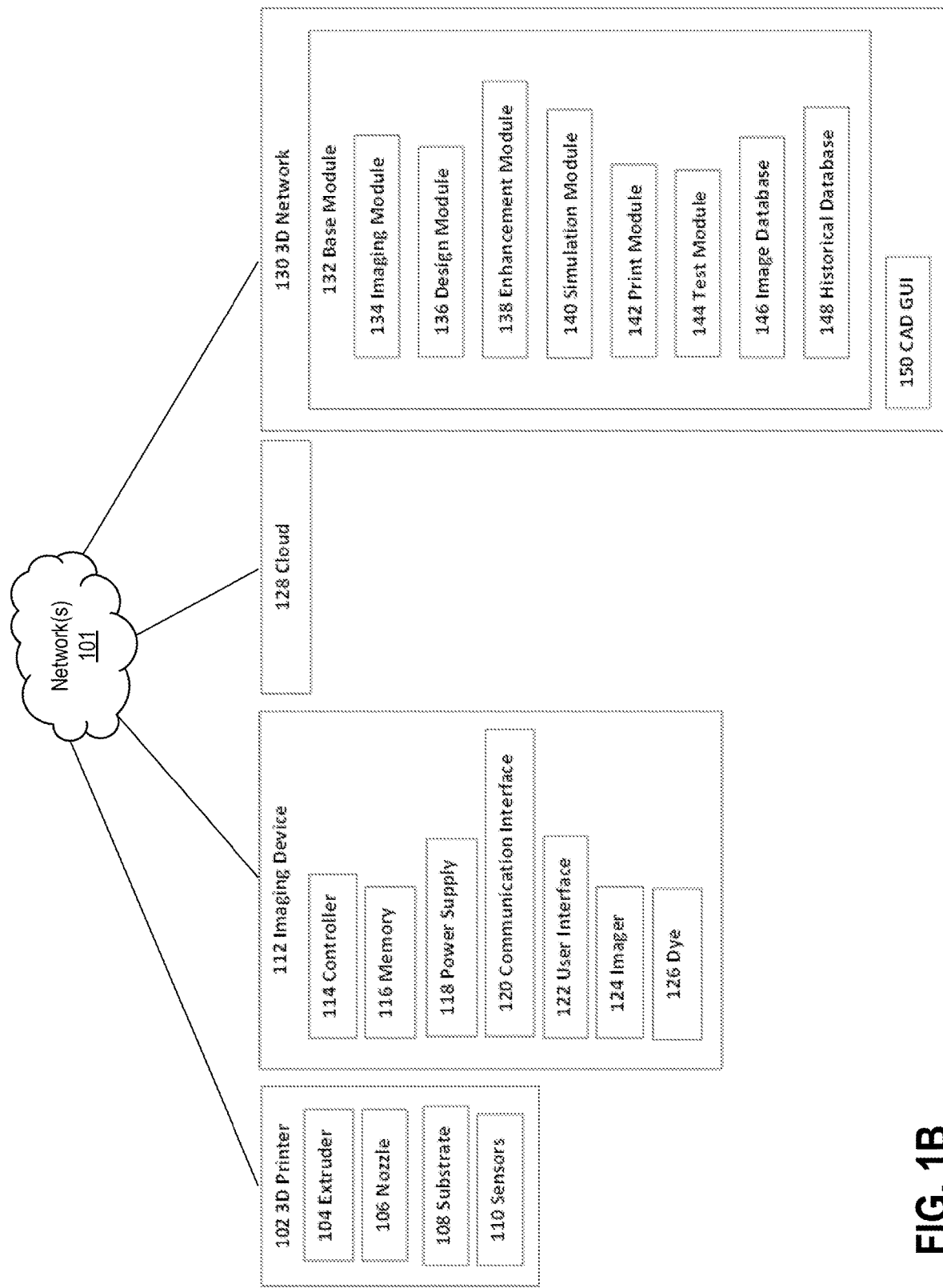
FIG. 1B is a system diagram of components that perform the disclosed techniques.

Referring to the figures, FIG. 1A is a conceptual diagram for designing and optimizing a 3D printed object to be inserted into an area of concern of a patient. A 3D network computing system 130, image database 146, historical database 148, imaging device(s) 112, user device GUI 150, and 3D printer 102 can communicate with each other (e.g., wired and/or wireless) via network(s) 101. Refer to FIG. 1B for further discussion about the components 130, 146, 148, 112, 150, 102, and 101.

Any one or more of the components 130, 146, 148, 112, 150, 102, and 101 can be remote from each other, integrated with each other, and/or part of a same computing environment and/or network. As shown in FIG. 1A, the 3D network computing system 130, the image database 146, and the historical database 148 are remote from each other and the other components described herein. The imaging device(s) 112 can be located in a medical facility 154. The 3D printer 102 can be located in a printing location 158. The user device GUI 150 can be located in a design location 160. In some implementations, the imaging device(s) 112 and the user device GUI 150 can be in a same location, such as the medical facility 154 or another medical location. As another example, the 3D printer 102 may also be located in the medical facility 154 such that, once an object is designed, the object can be printed by the 3D printer 102 and inserted into a patient during a medical procedure. One or more other variations in location of the components described herein is also possible.

As mentioned above, the medical facility 154 can include the imaging device(s) 112. A patient 152 can go to the medical facility 154 to have an area of concern imaged and/or diagnosed by a medical professional or other relevant user.

The design location 160 can include the user device GUI 150. A user 156 can interact with the GUI 150 to design, alter, enhance, optimize, test, and/or otherwise modify an object to be 3D printed and inserted into the patient 152's area of concern. The user 156 can be any relevant user, such as a medical professional, nurse, doctor, lab technician, object designer, etc.

The printing location 158 can include the 3D printer 102. The 3D printer 102 can be configured to automatically print the object to then be inserted into the patient 152's area of concern.

Still referring to FIG. 1A, the imaging device(s) 112 can image the area of concern of the patient 152 at the medical facility 154 (block A). Sometimes, the 3D network computing system 130 can transmit instructions to the imaging device(s) 112 that cause the imaging device(s) 112 to begin imaging the area of concern of the patient 152.

The captured image data can be transmitted from the imaging device(s) 112 to the 3D network computing system 130 and/or the image database 146 (block B). When stored in the image database 146, the 3D network computing system 130 can retrieve the image data to perform the techniques described below.

Using the image data, the 3D network computing system 130 can generate a 3D image of the area of concern of the patient 152 (block C). The 3D network computing system 130 can then transmit the 3D image to the user device GUI 150 in block D.

The user device GUI 150 can output the 3D image for presentation in a GUI display (block E). The user device can be any type of computing device, including but not limited to a laptop, tablet, computer, mobile phone, smartphone, monitor, or other computing system. The 3D image can be displayed at the GUI 150 with one or more selectable features to view, modify, alter, and/or enhance the 3D image. For example, the user 156 can adjust a size and/or shape of an object to be 3D printed and inserted into the area of concern represented in the 3D image. Accordingly, the user device GUI 150 can receive user input from the user 156 to adjust the object to be 3D printed for the area of concern (block F).

As an illustrative example, the patient 152 can have a weakened blood vessel that is limiting blood flow due to plaque buildup. An area of concern in the patient 152's body, which includes the weakened blood vessel, can be imaged (block A). The 3D network computing system 130 can generate a 3D image of the area of concern with the weakened blood vessel (block C), which can then be outputted at the user device GUI 150 (block E). The user 156 can determine that a stent or grafted blood vessel is required to resolve the health issue experienced by the patient 152. The user 156 can manipulate the 3D image representation of the weakened blood vessel that is outputted at the user device GUI 150 in order to change or alter physical dimensions, both internally and externally, of the area of concern, and more specifically the stent or grafted blood vessel that can be 3D printed and inserted into the area of concern (block F). The user 156's manipulation of the 3D image can be beneficial to improve and strengthen the weakened blood vessel to allow for more blood flow in the patient 152's body without compromising or otherwise harming the patient 152's body. As a result, a design of the stent or grafted blood vessel can be optimized to provide health benefits to the patient 152 and also to fit exactly into the space provided at the area of concern where the weakened blood vessel is located.

The user input can be transmitted to the 3D network computing system 130 (block D). The user input can be, for example, an altered 3D image of the area of concern. The 3D network computing system 130 can then retrieve relevant historic patient data (block G) and generate one or more recommendations for enhancing the altered 3D image based on the retrieved data (block H).

To retrieve the relevant historic patient data in block G, the 3D network computing system 130 can identify information about the patient 152 that is relevant to their health condition and therefore can be used as criteria to identify the relevant historic patient data. In the example of the patient 152 having a weakened blood vessel, the 3D network computing system 130 can retrieve historic patient data for (i) other patients of same or similar demographics as the patient 152, (ii) other patients having the same or similar weakened blood vessel, (iii) other patients who received stents or grafted blood vessels to replace the weakened blood vessel, (iv) other patients having the same or similar sizing, measurements, or other characteristics of the area of concern as the patient 152, (v) other patients who are healthy as a result of not having a weakened blood vessel, and/or (vi) other patients who are health as a result of having the weakened blood vessel replaced by the 3D printed stent or grafted blood vessel. One or more other criteria can be used to determine what historic patient data is relevant for the particular patient 152's condition.

Generating the recommendation(s) in block H can include identifying one or more image data in the retrieved historic patient data that may provide an optimized or otherwise enhanced design for the object to be 3D printed in comparison to the user-altered 3D image of the area of concern. In some implementations, generating the recommendation(s) can include combining one or more of the retrieved historic patient data in such a way that can provide an enhancement or improvement over the design for the object in the user-altered 3D image. In some implementations, generating the recommendation(s) can include identifying previous recommendations that had been made to and/or implemented for the other patients who had similar or same medical conditions as the patient 152. The generated recommendation(s) can provide ways or suggestions to improve design, strength, structure, and/or flexibility of the object to be 3D printed and inserted into the area of concern in the patient 152's body.

The recommendation(s) can be transmitted to the user device GUI 150 (block D) and outputted in the GUI display thereon. The user 156 can view the recommendation(s) and provide user input to enhance the altered 3D image based on their review of the recommendation(s) (block F). The enhanced 3D image can then be transmitted to the 3D network computing system 130 (block D).

The 3D network computing system 130 can simulate the 3D printed object based on the recommendation(s) and/or the user input in response to reviewing the recommendation(s) (block I). For example, the 3D network computing system 130 can run one or more simulations of the object to be 3D printed based on the enhanced 3D image. The simulations can include simulating a printing process of the object according to printing instructions, materials, and/or other information relevant for printing the object into its particular design, shape, dimensions, space in the patient 152's body, etc. The simulations can additionally or alternatively include simulating an implant process for inserting or otherwise implanting the object in the area of concern in the patient 152's body. The 3D network computing system 130 can run the simulation(s) to determine whether printing and/or implanting the object would be a success (or likely be successful) for the particular patient 152.

Simulation results can optionally be transmitted to the user device GUI 150 for presentation to the user 156 (block D). Optionally, the user 156 may further modify the 3D image based on the simulation results. The modified 3D image can be transmitted to the 3D network computing system 130 (block D) and the 3D network computing system 130 can generate new recommendations (block H) and/or run one or more additional simulations (block I) based on the modified 3D image. These operations can be repeated whenever the user 156 modifies, alters, and/or enhances the 3D image such that the design of the object to be 3D printed and inserted into the area of concern of the patient 152 can be optimized.

If a simulation is successful, the 3D network computing system 130 can execute instructions to 3D print the object (block J). The 3D network computing system 130 can transmit the instructions to the 3D printer 102 at the printing location 158. The 3D printer 102 can then print the object according to specifications for the object that are included in the instructions. The specifications can include information such as a type of material, biomaterial, and/or bio-ink to be used in printing the object, instructions on how to print the object, shape, size, and/or dimensions of the object, etc. These specifications can be determined by the 3D network computing system 130, based on the retrieved historic patient data (block G), provided by the user 156 at the user device GUI 150, based on the generated recommendations (block H), based on the simulation results (block I), based on the 3D image that has been altered and/or enhanced by the user 156 (block F), based on patient specific data for the patient 152, and/or other information.

As described further below, once the object is 3D printed, the object can be inserted into the patient 152 at the area of concern. Additionally or alternatively, one or more tests can be run on the printed object. The tests can be performed by the user 156 and/or automatically by the 3D network computing system 130 or another computing system and/or device. The tests can be used to test strength, functionality, and/or performance of the 3D printed object. If the object passes one or more of the tests, then the object can be inserted into the patient 152 at the area of concern. If the object does not pass the test(s), the object may not be inserted into the patient 152. Instead, the user 156 can be prompted to make a new design for the object, the 3D network computing system 130 can generate a suggested design or modifications to the design of the object, and/or one or more of the blocks A-I described herein can be repeated in order to optimize design, printing, and insertion of the 3D printed object for the particular patient 152.

FIG. 1B is a system diagram of components that perform the disclosed techniques. A 3D printer 102, imaging device 112, cloud 128, and 3D network 130 can communicate (e.g., wired and/or wireless) via network(s) 101. The components 102, 112, 128, and 130 can be used to optimize 3D printed implants as described herein. The 3D printer 102 can be, for example, a 3D bioprinter, which may be a device capable of layer-by-layer additive robotic computer-aided bio fabrication of functional 3D organ constructs. The 3D printer 102 can use self-assembling tissue spheroids and a digital model in order to print the functional 3D organ constructs, or 3D printed implants as described throughout this disclosure.

3D bioprinting can be a process of using 3D printing technologies to assemble multiple cell types or stem cells/growth factors along with other biomaterials in a layer-by-layer fashion to produce bioartificial organs that maximally imitate their natural counterparts. In other words, bioprinting is a 3D printing of biological tissue and organs through the layering of living cells. For example, 3D bioprinting for fabricating biological constructs typically can involve dispensing cells onto a biocompatible scaffold using a successive layer-by-layer approach to generate tissue-like 3D structures. Some of the methods that are used for 3D bioprinting of cells can include, but are not limited to, photolithography, magnetic 3D bioprinting, stereolithography, and direct cell extrusion.

Bioprinters, such as the 3D printer 102, can have one or more components to perform the abovementioned techniques. Such components can include hardware, a type of bio-ink, and a material that is printed on biomaterials. Bio-ink can be a material made from living cells that behaves like a liquid, allowing relevant users to print with the ink in order to create a desired shape. To make bio-ink, a slurry of cells can be created that can be loaded into a cartridge and inserted into the 3D printer 102, along with another cartridge containing a gel known as bio-paper. For example, the liquid mixture of cells, matrix, and nutrients known as bio-inks can be placed in a printer cartridge and deposited using a patients' medical scans. When a bioprint is printed, pre-tissue can be transferred to an incubator, and this cell-based pre-tissue can then mature into a tissue.

In bioprinting, various types of printers can be used, including but not limited to inkjet, laser-assisted, and extrusion printers. Inkjet printers can mainly be used in bioprinting fast and large-scale products. For example, a type of inkjet printer, such as a drop-on-demand inkjet printer, prints materials in exact amounts, thereby minimizing cost and waste. Printers that utilize lasers provide high-resolution printing and extrusion printers print cells layer-by-layer, just like 3D printing to create 3D constructs. In addition to just cells, extrusion printers may also use hydrogels infused with cells.

In some implementations, the 3D printer 102 may be capable of mass-producing scaffold structures with a high degree of anatomical precision in scaffold products, allowing for creation of constructs that effectively resemble a microstructure of a natural organ or tissue structure. In some implementations, a patient's own cells may be used to increase likelihood of a successful organ transplant by reducing risk of rejection.

The 3D printer 102 can include various components, including but not limited to an extruder 104, a nozzle 106, a substrate 108, and/or one or more sensors 110. The extruder 104 can be configured to draw in, melt, and push out a biomaterial. For example, extrusion-based printing entails extruding, or forcing, a continuous stream of melted solid material or viscous liquid through a sort of orifice, often the nozzle 106 or a syringe. One or more types of bio-extrusion can include pneumatic-driven, piston-driven, and screw-driven. Pneumatic extrusion can use pressurized air to force liquid bio ink through a depositing agent. The air used to move the bio ink must be free of contaminants. Air filters can be used to sterilize the air before it is used. Piston-driven extrusion can use a piston connected to a guide screw. The linear motion of the piston squeezes material out of the nozzle. Screw-driven extrusion can use an auger screw to extrude biomaterial. The rotational motion can force the material down and out of the nozzle 106. Screw-driven devices may allow for use of higher viscosity materials and provide more volumetric control.

Once printed, many materials may require a crosslinking step to achieve the desired mechanical properties for the construct, which can be achieved for example with treatment of chemical agents or photo-crosslinkers. Another method of extrusion can therefore be direct extrusion, in which a pressurized force directs the bio-ink to flow out of the nozzle 106, and directly print the scaffold without any casting. The bio-ink itself for this approach can be a blend of polymer hydrogels, naturally derived materials such as collagen, and/or live cells suspended in the solution. In this manner, scaffolds can be cultured post-print and without a need for further treatment for cellular seeding. Indirect extrusion techniques for bioprinting, on the other hand, may require printing a base material of cell-laden hydrogels, but, unlike direct extrusion, can contain a sacrificial hydrogel that can be trivially removed post-printing through thermal or chemical extraction. The remaining resin solidifies and becomes the desired 3D-printed construct.

As mentioned above, the nozzle 106 can be the mechanical part of the 3D printer 102 that extrudes the biomaterial. The nozzle 106 conducts thermal energy provided by a heating cartridge and block to the biomaterial. Some focus in the use of direct printing techniques can be based upon use of coaxial nozzle 106 assemblies, or coaxial extrusion. The coaxial nozzle 106 setup can enable simultaneous extrusion of multiple material bio-inks, thereby capable of making multi-layered scaffolds in a single extrusion step. The development of tubular structures has also found the layered extrusion achieved via these techniques desirable for radial variability in material characterization that it can offer, as the coaxial nozzle provides an inner and outer tube for bio-ink flow.

The substrate 108 or biomaterial may be the material(s) adapted and used for printing 3D objects using the disclosed techniques. Some bioengineered substances may usually be stronger than the average bodily materials, including soft tissue and bone. These constituents can act as future substitutes, even improvements, for the original body materials. For example, alginate is an anionic polymer with many biomedical implications including feasibility, strong biocompatibility, low toxicity, and stronger structural ability in comparison to some of the body's structural material. Synthetic hydrogels may also be commonplace, including PV-based gels.

The sensors 110 may be used by the 3D printer 102 such as physical sensors, biosensors, chemical sensors, etc. For example, physical sensors may measure a physical quantity and convert that quantity into a signal to be read by an observer or an instrument, such as pressure sensors, displacement sensors, acceleration sensors, temperature sensors, flow sensors, resistance sensors, capacitive sensors, inductive sensors, electromagnetic sensors, thermoelectric sensors, photoelectric sensors. For example, biosensors may be used to detect presence of chemicals, such as enzyme-based, tissue-based, immunosensors, DNA biosensors, and thermal and piezoelectric biosensors. Chemical sensors may be measurement devices that convert a chemical or physical property of a specific analyte into a measurable signal, whose magnitude is normally proportional to the concentration of the analyte, which may be used to detect harmful toxins that may be created in the 3D printed object.

The imaging device 112 can be any device capable of collecting data used to create an image, or a representation, of a physical structure or phenomena. The imaging device 112 may include any device capable of detecting sound or electromagnetic waves and assembling a visual representation of the detected waves. Sometimes, multiple imaging devices may be used with the disclosed techniques. The imaging device 112 may collect waves from any part of the electromagnetic spectrum or sounds at any range of frequencies, often as a matrix of independently acquired measurements, with each representing a pixel of a 2D or 3D image. These measurements may be taken simultaneously or in series via a scanning process or a combination of methods. Some pixels of an image produced by the imaging device 112 may be interpolated from direct measurements representing adjacent pixels in order to increase resolution of a generated image. The imaging device 112 may also receive or generate imaging data from a plurality of imaging devices 112. The plurality of imaging devices 112 may include, for example, an MM, CT scan, X-ray, ultrasound, PET, etc. The imaging device 112 may also leverage any algorithm or software module capable of determining qualitative or quantitative data from medical images, which may be, for example, a deep learning algorithm that has been trained on a data set of medical images. Moreover, the imaging device 112 may acquire images in real-time and/or be used to create composite images or models in real-time.

The imaging device 112 can include multiple components, including but not limited to a controller 114, memory 116, power supply 118, communication interface 120, user interface 122, imager 124, and/or dye 126. The controller 114 may be a computing device having of a processor(s) for performing computations that communicates with a memory for storing data. The controller 114 can be in communication with the communications interface 120, for example, which can provide communication between components of the imaging device 112 and the other system components described in FIG. 1B. The controller 114 may be a commercially available central processing unit (CPU) or graphical processing unit (GPU) or may be a proprietary, purpose-build design. More than one controller 114 may operate in tandem and may be of different types, such as a CPU and a GPU. A GPU may not be restricted to only processing graphics or image data and may also be used for other computations. The controller 114 may receive tasks or actions from the external 3D network 130, such instructions to take images using the imaging device 112.

The memory 116 can be an electronic circuitry within a computing device that temporarily stores data for usage by the controller 114. The memory 116 may comprise persistent data storage for storing data used by the controller 114. The memory 116 may be integrated into the controller 114 or may be a discrete component. The memory 116 may be integrated into a circuit, such as soldered on component of a single board computer (SBC) or may a removable component such as a discrete dynamic random-access memory (DRAM) stick, secure digital (SD) card, flash drive, solid state drive (SSD), magnetic hard disk drive (SSD), etc. In some embodiments, the memory 116 may be part of the controller 114. Multiple types of memory 116 may be used by the imaging device 112.

The power supply 118 can be a hardware component that supplies power to the imaging device 112. The power supply 118 may receive power from an electrical outlet and convert the current from AC, alternating current, to DC, direct current. The power supply 118 may also regulate the voltage to an adequate amount, which allows the imaging device 112 to run smoothly without overheating.

The communication interface 120 may provide a wireless network. The communication interface 120, if wireless, may be implemented using communication techniques such as Visible Light Communication (VLC), Worldwide Interoperability for Microwave Access (WiMAX), Long Term Evolution (LTE), Wireless Local Area Network (WLAN), Infrared (IR) communication, Public Switched Telephone Network (PSTN), Radio waves, and other communication techniques known in the art. The communication interface 120 may allow ubiquitous access to shared pools of configurable system resources and higher-level services that can be rapidly provisioned with minimal management effort, often over Internet and relies on sharing of resources to achieve coherence and economies of scale, like a public utility, while third-party clouds enable organizations to focus on their core businesses instead of expending resources on computer infrastructure and maintenance.

The user interface 122 may accept inputs from users and/or provide outputs to the users. A user can, for example, interact with the user interface 122 using one or more user-interactive objects and devices. The user-interactive objects and devices may including, but are not limited to, user input buttons, switches, knobs, levers, keys, trackballs, touchpads, cameras, microphones, motion sensors, heat sensors, inertial sensors, touch sensors, or a combination of the above. Further, the user interface 122 may be implemented as a Command Line Interface (CLI), a Graphical User Interface (GUI), a voice interface, or a web-based user-interface. The user interface 122 may be operated by the user to determine power requirements for the imaging device 112 and/or to send tasks to the imaging device 112, such as capturing images of the patient's damaged body part.

The imager 124 can also be a camera, which may be a component of the imaging device 112. The imager 124 can produce images, such as images captured by an MM machine, CT scanner, X-ray machine, etc. The images can then be used by the 3D network 130 to produce diagnostic images of the patient's body.

The dye 126, such as a contrast dye, can be a substance that, when injected into the patient's body, allows a radiologist to see an internal structure of concern in the patient's body in greater detail. The dye 126 can make the internal structure more visible against a background of other tissues. The imaging device 112 can be configured to automatically control when the dye 126 is injected into the patient's body and a quantity of the dye 126 injected therein. Therefore, when imaging is taken using a contrast dye, scans may better represent organs, ligaments, tendons, blood vessels, bones, or nerves of the patient.

The cloud 128 can be a distributed network of computers including servers and databases. The cloud 128 may be a private cloud, where access is restricted by isolating the network, such as preventing external access, or by using encryption to limit access to only authorized users. Alternatively, the cloud 128 may be a public cloud where access is widely available via the Internet. The public cloud may not be secured or may be include limited security features. The cloud 128 can be configured to perform one or more of the operations described herein. The cloud 128 can also be configured to store one or more data described throughout this disclosure. Furthermore, the cloud 128 can be configured to establish and/or facilitate communication and connectivity between one or more components described herein, such as the 3D network 130 and the imaging device 112.

The 3D network 130 can be a computing system and/or computer network configured to perform the techniques described herein. The 3D network 130 can include a base module 132, an imaging module 134, a design module 136, an enhancement module 138, a simulation module 140, a print module 142, a test module 144, an image database 146, a historical database 148, and/or a CAD GUI 150. Sometimes, one or more components, such as the components 134, 136, 138, 140, 142, 144, 146, and 148 can be part of the base module 132. The 3D network 130 can be configured to collect the patient imaging data from the imaging device 112, create a 3D image to be used in the CAD GUI 150, provide interactive GUIs for a relevant user, such as a medical professional, to design improvements to the 3D image of an implant to be made for the patient, allow for the user to enhance the 3D image using historical image data, perform simulations on the enhanced 3D image, execute printing of the 3D image by sending instructions to the 3D printer 102 and monitoring the printing process, and allowing the user to test the printed 3D implant. The 3D printed implant can include, but is not limited to, a stent, organ, blood vessel, cartilage, bone, etc.

Referring to the components of the 3D network 130, the base module 132 can initiate the imaging module 134, the design module 136, the enhancement module 138, the simulation module 140, the print module 142, and/or the test module 144. The base module 132 can additionally or alternatively determine whether a simulation is successful and/or determine whether a test was successful for the 3D printed object to be used for the specific patient.

The imaging module 134 can be configured to communicate with the imaging device 112. The imaging module 134 can optionally send instructions to the imaging device 112 to begin capturing image data of the patient. The imaging module 134 can then receive the patient images from the imaging device 112. The imaging module 134 can store the patient images in the image database 146. The imaging module 134 can also generate/create a 3D image of the patient, which can also be stored in the image database 146. For example, the imaging module 134 can utilize computed tomography (CT). High-resolution 3D images of the patient's anatomy can be obtained by compiling a series of X-ray images captured at various angles. The imaging module 134 can utilize magnetic resonance imaging (MM), and can utilize magnetic fields and radio waves where MIII can provide detailed 3D images of soft tissues and bone structures. The imaging module 134 can utilize ultrasound, and sound waves can create real-time, non-invasive 3D images of the patient's internal structures, that can in some implementations be utilized for visualizing soft tissues The imaging module 134 can utilize 3D Surface Scanning, and optical devices can capture the external contours of the patient's body, generating a 3D representation of the surface anatomy. The imaging module 134 can utilize positron emission tomography (PET) that can be combined with CT or MIII PET and allow for functional imaging and precise localization of areas requiring implantation. The imaging module 134 can utilize any combination of the CT, MIII, Ultrasound, 3D surface scanning, PET, or other imaging techniques.

The imaging module 134 can generate the three-dimensional objects by utilizing three-dimensional object generation techniques. For example, imaging module 134 can utilize image segmentation, isolating the region of interest in medical images, creating a 3D model of the target area for implant customization. In another example, imaging module 134 can utilize surface reconstruction, converting segmented 2D images into a 3D surface model using techniques like Marching Cubes or Delaunay triangulation. Imaging module 134 can utilize volumetric modeling, generating 3D models by stacking segmented 2D slices, providing a detailed representation of the patient's internal structures. Imaging module 134 can utilize parametric modeling, using mathematical equations and patient-specific parameters to define a 3D model of the implant, allowing for precise customization. Imaging module 134 can utilize generative design implementing algorithms and optimization techniques to automatically generate patient-specific implant designs based on specific criteria, such as biomechanical properties and tissue compatibility. The imaging module 134 can then transmit a notification to the base module 132 indicating that image capture and 3D image generation is complete.

Next, the base module 132 can then trigger activation of the design module 136. The design module 136 can be configured to extract/retrieve the patient's 3D image from the image database 146. The design module 136 can display the 3D image at the CAD GUI 150. The 3D image can be editable by the user using one or more input devices. For example, the user can alter the 3D image. For example, the user can alter the 3D image to accommodate for the patient anatomy by adjusting the implant design to better fit the patient's unique anatomical features. The user can alter the strength and functionality of the 3D image, where the user can modify the implant's properties, such as weight, material composition, or shape, to enhance its performance, durability, and compatibility with surrounding tissues. In some embodiments, the user can be limited from making alterations that negatively impact the implant's function or range of motion, making changes that could harm the patient's anatomy, such as creating sharp edges or protrusions, making alterations that could compromise the implant's sterility or encourage bacterial growth may be restricted, users may be prevented from making changes that could weaken the implant, leading to breakage, binding, or malfunction. In some embodiments, the design module may suggest alterations based on predefined criteria, which the practitioner can review and approve. In other embodiments, if a practitioner proposes an alteration that the design module deems unsafe, the module may reject it and suggest an alternative solution that achieves a similar goal while adhering to safety parameters. The design module 136 can then store the altered image in the image database 146 in association with data about the particular patient. The design module 136 can then transmit a notification to the base module 132 indicating completion of the operations mentioned above.

The base module 132 can then initiate the enhancement module 138. The enhancement module 138 can be configured to retrieve the altered 3D image from the image database 146 and then compare the altered 3D image to images stored in the historical database 148. The enhancement module 138 can determine one or more recommendations. For example, the recommendations can relate to strength enhancements, e.g., recommending material or design changes to improve the implant's durability and longevity. The recommendations can relate to enhancing range of motion, e.g., suggesting alterations to the implant's shape or design to promote better joint mobility. The recommendations can relate to decreased weight, e.g., recommending the use of lighter materials or optimized design to reduce the implant's overall weight. The recommendations can relate to making the implant suitable for less invasive installation, e.g., suggesting design changes that simplify the size and shape of the implant, resulting in a less invasive implantation procedure for the patient.

In some embodiments, the enhancement module 138 compares the altered 3D image to images from similar procedures (e.g., procedures involving the same joint, same patient age/sex, weight, etc.) to assess the proportionality of the implant, strength of the implant, range of motion, and compatibility with the patient's anatomy. The enhancement module 138 retrieves information based on similarity between patient data, prioritizing the closest match for factors such as age, sex, weight, height, and any other relevant characteristics. The enhancement module 138 may also display the altered 3D image and the image recommendation(s) at the CAD GUI 150, to be reviewed by the user. Once the user views this information, the user can further enhance the altered 3D image using any of the recommended images. The enhancement module 138 then stores the enhanced image in the image database 146 in association with the patient's information. The enhancement module 138 can return a notification to the base module 132 indicating that the abovementioned operations have been completed.

The base module 132 can next initiate the simulation module 140. The simulation module 140 can be configured to retrieve the enhanced 3D image from the image database 146. The simulation module 140 can perform a simulation on the enhanced 3D image. In some embodiments, the simulation includes creating a virtual representation of the 3D printed implant inside the patient's body to analyze its performance under various conditions. The simulation module 140 simulates a plurality of conditions that may impact implant success, such as physical forces, stress and strain on the implant, changes in patient weight/height/age, and other health conditions that may affect the implant (e.g., scar tissue, vascularity). In some embodiments, the simulation module 140 can evaluate object printing feasibility, where the design or enhancement module evaluates the feasibility of 3D printing the implant, as established in the field. In some embodiments, the simulation module may simulate the insertion process, particularly in cases where robotically assisted surgery is used. The module can simulate a surgical robot performing a portion of the procedure.

In some embodiments, the simulation module 140 simulates outcomes from implant insertion, such as projected recovery time, implant lifecycle (including potential repair or replacement needs), and potential limitations or improvements in the patient's lifestyle as a result of the implant. The simulation module 140 can determine whether the simulation was successful or unsuccessful based on one or more metrics. In some examples, the metrics can relate to patient safety and ensuring that the implant poses minimal risk to the patient, does not cause harm, and/or adheres to established safety standards. As another example, one or more of the metrics can relate to biocompatibility. The implant is preferably made from materials that are compatible with the patient's body to minimize adverse reactions, such as inflammation, infection, or rejection. The metrics can relate to implant functionality in another example. The success of the implant depends on its ability to restore or improve the patient's normal function, such as range of motion, strength, and stability. The metrics can relate to durability and longevity: a successful implant should be able to withstand the stresses and strains of daily use over an extended period without degradation or failure. The metrics can relate to patient satisfaction: the implant should result in an improved quality of life for the patient, including reduced pain, better mobility, and enhanced overall well-being. The metrics can relate to ease of implantation: a successful implant should be easily inserted during the surgical procedure, with minimal complications and a reduced risk of errors. The metrics can relate to recovery time: the implant should contribute to a faster and smoother recovery process for the patient, with minimal postoperative complications; The metrics can relate to cost-effectiveness: the implant should offer a good balance between performance, durability, and affordability, making it accessible to a wide range of patients. In some implementations, one or more of these metrics can be weighted by a practitioner and/or algorithm to classify whether the implant is "successful" or "unsuccessful" for a given patient. If it is determined that the simulation is unsuccessful, the simulation module 140 can transmit a signal to the base module 132 indicating that the simulation was unsuccessful. If it is determined that the simulation was successful, the simulation module 140 can transmit a signal to the base module 132 indicating that the simulation was successful.

The print module 142 can then be initiated by the base module 132. The print module 142 can be configured to retrieve the enhanced image from the image database 146 based on the simulation module 140 providing an indication that the simulation was successful. The print module 142 can establish a connection to the 3D printer 102. The print module 142 can then send the enhanced image to the 3D printer 102 with instructions for printing the 3D printed object according to the enhanced image. The print module 142 can therefore trigger the 3D printer 102 to print the enhanced image as the 3D printed object. The print module 142 can continuously poll the 3D printer 102 for a print completion signal in order to monitor progress of the 3D printing process. Once the print module 142 receives the print completion signal from the 3D printer 102, the print module 142 can transmit an indication of such to the base module 132.

Next, the test module 144 can be initiated by the base module 132. The user can test the 3D printed object. For example, before inserting the 3D printed implant into the patient, the practitioner can conduct several tests to ensure its performance, safety, and quality. Some of these tests may include: Physical measurements: The practitioner checks the dimensions of the implant to confirm that it matches the intended design and is suitable for the patient's unique anatomy; Range of motion: The practitioner tests the implant's range of motion to ensure that it allows for proper joint movement and meets the functional requirements; Surface examination: The practitioner inspects the implant's surface and features for any irregularities, such as gaps or defects in the material, which could affect its performance or safety; Material composition: The practitioner verifies that the implant is made from the appropriate biocompatible materials to minimize the risk of adverse reactions or implant failure; Mechanical testing: The implant may undergo stress and strain tests to evaluate its durability and ability to withstand the forces it will experience once implanted; Sterilization: The practitioner ensures that the implant has been properly sterilized to minimize the risk of infection during the surgical procedure; Compatibility with imaging techniques: The practitioner may test the implant's compatibility with various imaging modalities, such as X-ray, MM, or CT scans, to ensure that future imaging studies can be conducted without interference. Subsequent to these tests and examinations confirming the implant's safety, quality, and functionality the practitioner can proceed with inserting the implant into the patient.

The test module 144 can determine whether the test is successful or unsuccessful. The test module 144 can use a set of predefined criteria and tolerances to evaluate the success of each test conducted by the practitioner. To determine whether the test is successful or not, the module performs the following steps: Test metrics input: The practitioner inputs the test metrics obtained from their physical examination, mechanical testing, and any other relevant assessments; Compare with predefined criteria: The module compares the input test metrics to the predefined criteria and tolerances specific to the implant type, patient profile, and intended function. These criteria may include acceptable ranges for dimensions, range of motion, material properties, surface quality, and other factors affecting implant performance and safety; Evaluate success: The module evaluates each test metric against the corresponding predefined criteria. If the metric falls within the acceptable range or tolerance, the test is considered successful for that aspect; Overall test success: The module determines the overall success of the implant testing by analyzing the individual test results. If all tests meet the predefined criteria and tolerances, the module deems the implant successful and suitable for insertion into the patient; Feedback and recommendations: If any test metric falls outside the acceptable range or tolerance, the module may provide feedback to the practitioner, identifying the issue and suggesting potential modifications or adjustments to improve the implant's performance and safety.

If it is determined that the test was unsuccessful, the test module 144 can transmit a signal to the base module 132 that the test was unsuccessful. If it is determined that the test was successful, the test module 144 can transmit a signal to the base module 132 indicating that the test was successful.

As described above, the image database 146 can be configured to contain patient medical imaging data that is collected by the imaging module 134 and generated by the imaging device 112. The image database 146 can also store 3D images that are generated for each patient, altered 3D images, and enhanced 3D images for each patient. The database 146 can also maintain such data in association with each patient. Additional data can be stored for each patient, including but not limited to a patient ID, regions of the patient's body that the images capture, type or types of images captured (e.g., MM, CT scan, X-ray, ultrasound, PET), a 3D image data file, an altered 3D image data file, and/or an enhanced 3D image data file.

The historical database 148 can store historical patient medical imaging data, which can be used by the enhancement module 138 to enhance the altered 3D image. The database 148 can contain data associated with healthy patients, which may be used as recommendations for enhancing a current or particular patient's 3D printed object (e.g., a stent, blood vessel, tissue, organ, cartilage, bone). The historic patient data can be stored in association with the corresponding patient IDs, the regions of the body that the images capture, and the type or types of images captured.

As described above, the CAD GUI 150 can be a user interface as part of a computer software system used by the relevant user (e.g., medical professional). The CAD GUI 150 can provide user interfaces for designing 3D printed objects for patients. CAD output can often be in the form of electronic files used for print, machining, or other manufacturing operations. In some implementations, the user can interact with the CAD GUI 150 using one or more user-interactive objects and devices. The user-interactive objects and devices may include, for example, user input buttons, switches, knobs, levers, keys, trackballs, touchpads, cameras, microphones, motion sensors, heat sensors, inertial sensors, touch sensors, or a combination of any of the above. The CAD GUI 150 may allow the user to view and interact with a body part of the patient that requires replacement in a 3D space. The CAD GUI 150 can also allow the user to alter, adjust, enhances, etc. the 3D image of the patient's body part, or any aspect of the patient's body to optimize 3D printing and/or design of the object to be inserted into the patient's body to replace the damaged body part. The user's adjustments or alterations may be stored in the image database 146 as described above. In some implementations, the user may store multiple iterations of the altered 3D image for the patient. In some implementations, multiple users can be designing, altering, and/or enhancing the original 3D image of the patient's body part. The disclosed technology can therefore facilitate collaboration amongst the multiple users so that an optimized design of the 3D printed object for the particular patient can be generated, printed, and inserted into the patient.

Figure 2:
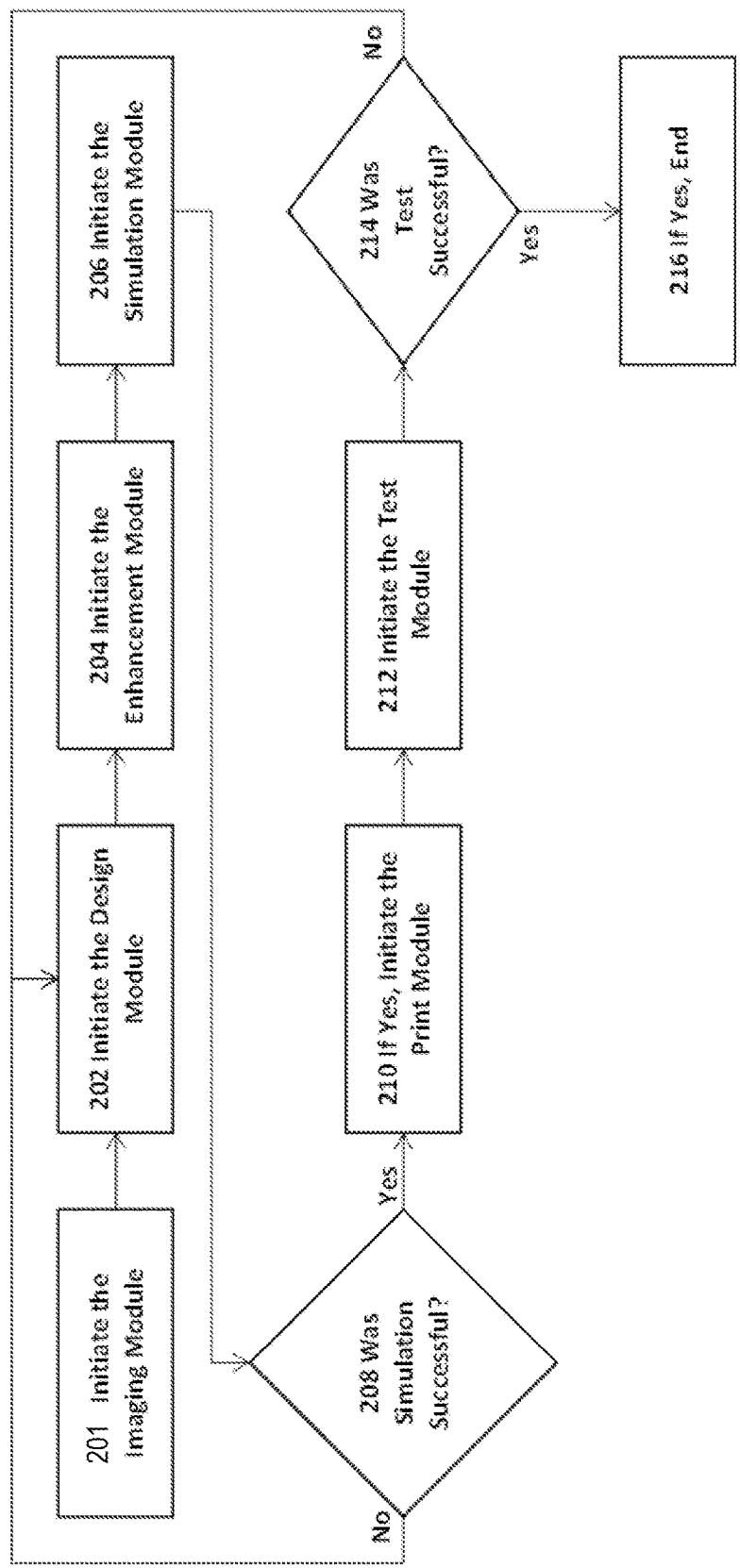
FIG. 2 is a flowchart of a process for designing and optimizing a 3D printed implant for a patient.

FIG. 2 is a flowchart of a process 200 for designing and optimizing a 3D printed implant for a patient. The process 200 can be performed by the base module 132 of FIG. 1B. One or more other components described herein can also be configured to perform one or more blocks in the process 200. For illustrative purposes, the process 200 is described from the perspective of the base module 132. In some implementations, the blocks performed in the process 200 may be implemented in differing order. Furthermore, the outlined blocks are only provided as examples, and some of the blocks may be optional, combined into fewer operations, or expanded into additional operations without detracting from the essence of the disclosed embodiments.

Referring to the process 200, the base module 132 initiates, at block 201, the imaging module 134. This initiation can include transmitting instructions to the imaging module 134 that causes the imaging module 134 to establish a connection with the imaging device 112. The imaging module 134 can then receive patient images from the imaging device 112 as the images are captured/generated by the imaging device 112. As described above, the imaging module 134 stores the patient images in the image database 146. The imaging module 134 also can create a 3D image for the patient based on the received patient images.

The base module 132 initiates, at block 202, the design module 136, based on receiving an indication from the imaging module 134 that imaging and/or 3D image generation is complete. The design module 136 can retrieve the patient's 3D image from the image database 146 and/or receive the 3D image from the imaging module 134 and/or the base module 132. The design module 136 can be configured to display the 3D image at the CAD GUI 150. The user can provide user input at the CAD GUI 150 to alter the 3D image. The design module 136 can apply the user input to the 3D image in order to alter the image. The altered image can then be stored, by the design module 136, in the image database 146. The design module 136 returns to the base module 132.

The base module 132 initiates, at block 204, the enhancement module 138. The enhancement module 138 retrieves the altered 3D image from the image database 146. The enhancement module 138 compares the extracted altered 3D image to images stored in the historical database 148. The enhancement module 138 determines recommendations from the historical database 148 that can be used to enhance or otherwise improve/change a design, print, and/or installment of a 3D printed object that is to be inserted into the patient's body. The enhancement module 138 displays the extracted altered 3D image and the image recommendations at the CAD GUI 150. The user can also provide user input at the CAD GUI 150 to enhance the extracted altered 3D image based on the recommended images. The enhancement module 138 stores the enhanced image in the image database 146. The enhancement module 1389 then can return to the base module 132.

The base module 132 initiates, at block 206, the simulation module 140. The simulation module 140 can retrieve the enhanced 3D image from the image database 146. The simulation module 140 performs a simulation on the extracted enhanced 3D image from the image database 146. The simulation module 140 determines if the simulation was successful or unsuccessful. If it is determined that the simulation is unsuccessful, the simulation module 140 sends a signal to the base module 132 that the simulation was unsuccessful. If it is determined that the simulation was successful, the simulation module 140 sends a signal to the base module 132 that the simulation was successful. The simulation module 140 returns to the base module 132.

The base module 132 determines, at block 208, if the simulation was successful. For example, the simulation module 140 sends the base module 132 a signal if the simulation was unsuccessful and the process 200 returns to initiating the design module 136. If the simulation was successful, the simulation module 140 sends the base module 132 a signal that the simulation was successful, and the process 200 continues to initiate the print module 142.

As mentioned above, if it is determined that the simulation was successful, the base module 132 initiates, at block 210, the print module 142. The print module 142 can retrieve or receive the enhanced image. The print module 142 can establish a connection to the 3D printer 102. The print module 142 can then send the enhanced image to the 3D printer 102 with instructions to 3D print an object according to the enhanced image. The print module 142 can continuously poll for a print completion signal from the 3D printer 102. The print module 142 can receive the print completion signal from the 3D printer 102 when the object has been printed. The print module 142 can then return to the base module 132.

The base module 132 initiates, at block 212, the test module 144. The user can test the 3D printed object. The test module 144 determines if the test was successful or unsuccessful. If it is determined that the test was unsuccessful, the test module 144 can transmit a signal to the base module 132 indicating that the test was unsuccessful. If it is determined that the test was successful, the test module 144 sends a signal to the base module 132 that the test was successful. The test module 144 returns to the base module 132.

The base module 132 determines, at block 214, if the test was successful. For example, the base module 132 receives a signal from the test module 144 if the test was successful or unsuccessful. If it is determined that the test was unsuccessful, the base module 132 returns to initiating the design module 136 (block 202). If it is determined that the test was successful, the process can end at block 216.

Figure 3:
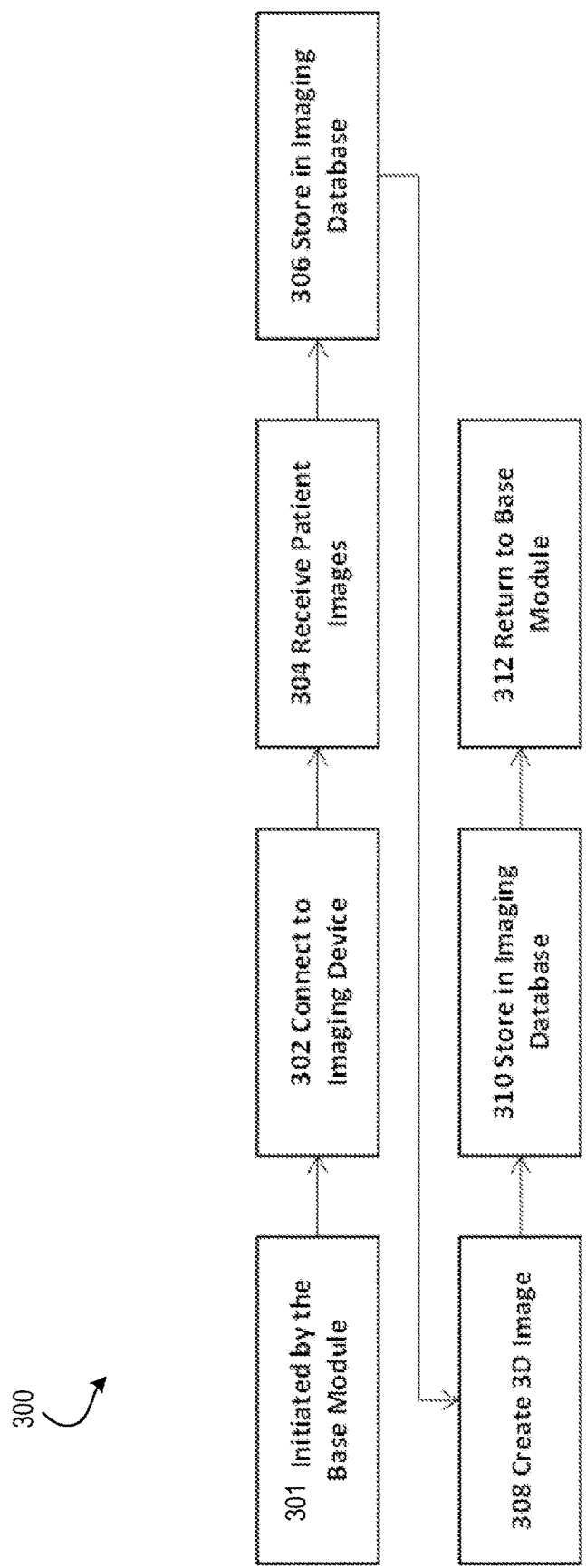
FIG. 3 is a flowchart of a process for imaging a patient's body for purposes of designing and optimizing a 3D printed implant for the patient.

FIG. 3 is a flowchart of a process 300 for imaging a patient's body for purposes of designing and optimizing a 3D printed implant for the patient. The process 300 can be performed by the imaging module 134 of FIG. 1B. One or more other components described herein can also be configured to perform one or more blocks in the process 300. For illustrative purposes, the process 300 is described from the perspective of the imaging module 134. In some implementations, the blocks performed in the process 300 may be implemented in differing order. Furthermore, the outlined blocks are only provided as examples, and some of the blocks may be optional, combined into fewer operations, or expanded into additional operations without detracting from the essence of the disclosed embodiments.

The process 300 begins with the imaging module 134 being initiated, at block 301, by the base module 132, as described above. The imaging module 134 establishes a connection (e.g., wired and/or wireless), at block 302, with the imaging device 112. For example, the imaging module 132 connects to the imaging device 112 through the communication interface 120 and via the cloud 128. The connection may comprise a handshake protocol in which the base module 132 (or the imaging module 134) initiates the connection and sends a message to the imaging device 112, the imaging device 112 then sending a response to the base module 132 that the connection has been established.

The imaging module 134 receives, at block 304, patient images. For example, the imaging module 134 receives the patient images, such as MM, CT scan, X-ray, ultrasounds, PET, etc., that are captured by the imaging device 112 in real-time, near real-time, and/or some threshold amount of time after the images are captured.

The imaging module 134 stores, at block 306, the patient images in the image database 146.

The imaging module 134 creates, at block 308, a 3D image. For example, the imaging module 134 uses the patient's images to create a 3D image of an area of concern for the patient, for example, a blood vessel in the leg, an artery connecting to the heart, a disc in the back, a bone in the arm, etc. The images taken by the imaging device 112 can be all different types of images (e.g., MRI, CT scan, PET) from various points of view. Using image processing techniques, the imaging module 134 can stitch these images together to create the 3D image or model of the area of concern for the patient that is captured in the images. The 3D image may be created using an optic technique in which two or more images of the same object are blended into one, thereby giving a 3D appearance to the single image. The images may be aligned by first identifying unique features that can act as a form of registration for aligning the images, such as anatomical structures, blood vessels, etc. Alternatively, registration markers may be artificial, such as physical elements added to the skin or surgically embedded to act as registration markers in the images.

Since many images of the area of concern can be captured from many different viewpoints (e.g., angles), the 3D image can also provide 3D views of the area of concern from the different viewpoints. As a result, the user may rotate, flip, zoom in or out, etc. of the 3D image using the CAD GUI 150 described herein. The user can change their perspective of the area of concern using the 3D image, which can facilitate the user's analysis and design of an object to be 3D printed for the area of concern of the patient. In some implementations, the 3D image can be made up of slices that allow for the user to navigate through an internal structure of anatomical structures represented by the 3D image.

The imaging module 134 stores, at block 310, the 3D image in the image database 146. The 3D image can be stored in association with the particular patient having the area of concern. The 3D image can be stored as a data file allowing the user (or any other user or multiple users) to review, alter, enhance, etc. the 3D image using the input tools provided by the CAD GUI 150.

Once complete with the blocks 301-310, the imaging module 134 can return a notification, at block 312, to the base module 132 indicating that the process 300 has been completed.

Figure 4:
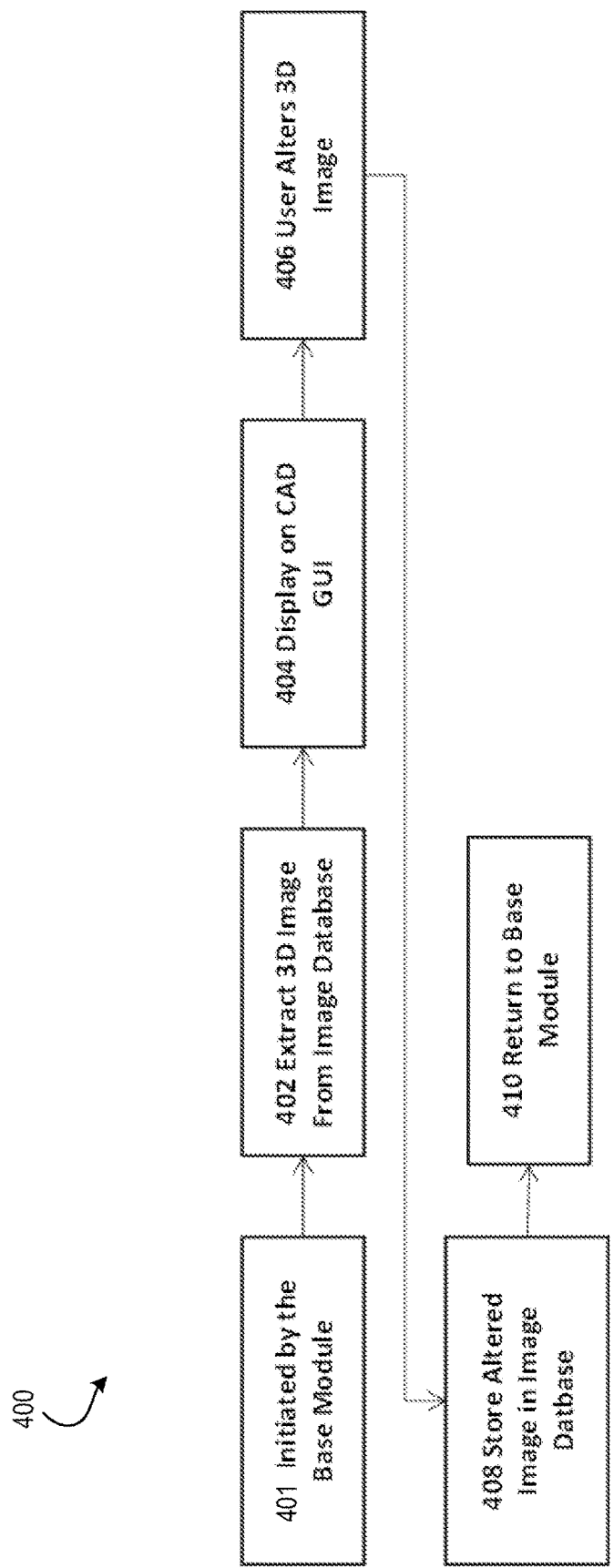
FIG. 4 is a flowchart of a process for designing a 3D printed implant for a patient.

FIG. 4 is a flowchart of a process 400 for designing a 3D printed implant for a patient. The process 400 can be performed by the design module 136 of FIG. 1B. One or more other components described herein can also be configured to perform one or more blocks in the process 400. For illustrative purposes, the process 400 is described from the perspective of the design module 136. In some implementations, the blocks performed in the process 400 may be implemented in differing order. Furthermore, the outlined blocks are only provided as examples, and some of the blocks may be optional, combined into fewer operations, or expanded into additional operations without detracting from the essence of the disclosed embodiments.

The process 400 begins with the design module 136 being initiated, at block 401, by the base module 132. The design module 136 extracts, at block 402, the patient's 3D image from the image database 146. In some implementations, the 3D image may be an exact replica of the area of concern (e.g., damaged body part) of the patient, with size, shape, and other measurements having same or similar ratios of the real body part or area of concern. This information can be useful to assist the user in designing, altering, and/or optimizing an object to be 3D printed for the area of concern.

The design module 136 displays, at block 404, the 3D image at the CAD GUI 150. The 3D image can be displayed with tools that the user can use to view, alter, adjust, change, etc., an appearance of the 3D image. The user may rotate, flip, zoom in or out, etc., the 3D image using the CAD GUI 150 to change their perspective of the 3D image. When the user changes their perspective of the area of concern represented by the 3D image, the user can also provide input at the CAD GUI 150 to alter the 3D image.

Accordingly, the design module 136 can receive user input indicating alterations that the user makes to the 3D image in block 406. For example, if the patient has a weakened blood vessel that is limiting blood flow due to plaque building up, the patient may require a stent or grafted blood vessel to resolve this issue. The 3D image may represent the current blood vessel, which is weakened and limiting blood flow. Upon viewing the 3D image, the user may change or alter physical dimensions, both internally and externally, of the blood vessel represented in the 3D image in order to strengthen the blood vessel and allow more flow, while also maintaining the area in which a 3D printed blood vessel or stent will be placed. In other words, the stent or newly-altered blood vessel will be able to be located in the same space as the previous blood vessel without taking up additional space.

In some implementations, the user may be able to simulate insertion of a stent into the blood vessel via the CAD GUI 150 to determine if a best course of action is to put a stent inside the patient as opposed to a new blood vessel or artery. Another example, may be if the patient requires a lumbar disc replacement that entails replacing a damaged disc with an artificial disc. The user may be able to view, alter, change, adjust, etc. the current 3D image of the damaged disc to create and design a healthy, structurally sound, flexible disc to be used as the artificial replacement. The user may make alterations to the current 3D image without changing the total space or area that the current disc requires, thereby allowing the new artificial disc to fill the exact void left inside the patient's body once the damaged disc is removed. In some implementations, the user may adjust the current 3D image of the patient's tissue, such as skin tissue, cartilage, such as a nose, ears, joints, etc., or bone, such as the radius, ulna, femur, tibia, fibula, etc.

The altered 3D image can include a virtual representation of a physical apparatus that may be 3D printed and inserted into the patient in order to achieve an altered physiology for the patient. For example, the physical apparatus may be a custom stent or a blood vessel, 3D printed or acquired from a donor. By modeling the physical apparatus in the 3D image, the design module 136 can determine exact dimensions, measurements, and/or other specifications to be able to 3D print the physical apparatus. These exact dimensions, measurements, and/or other specifications can then be used to accurately and precisely build the physical apparatus and safely insert the physical apparatus into the patient to resolve the patient's health issue. For example, a lumbar disc replacement may be designed by the user in the CAD GUI 150. Once designed, the design module 136 can determine exact dimensions and specifications required to 3D print the artificial lumbar disc.

The design module 136 stores, at block 408, the altered image in the image database 146. The altered image can be stored with the exact dimensions, specifications, and other measurements used for 3D printing the particular object to be inserted into the patient. For example, once the user is complete making adjustments or alterations to the patient's current 3D image, the altered 3D image is stored in the image database 146. A data file that contains the 3D image may also contain the specifications of the object such as measurements, ratio, size, etc. of the 3D object to allow for the object represented by the 3D image to be printed via the 3D printer 102. The design module 136 returns, at block 410, to the base module 132, upon completion of the process 400.

Figure 5:
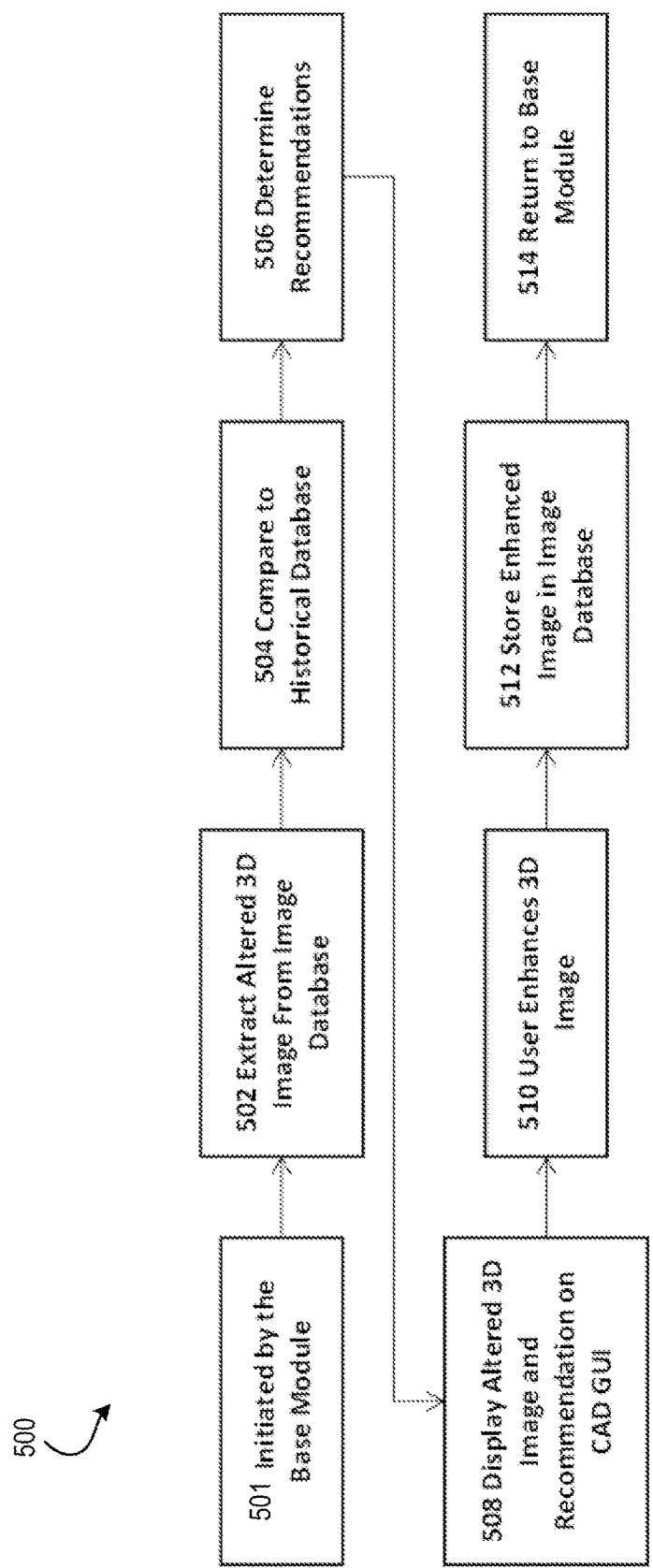
FIG. 5 is a flowchart of a process for improving the design of the 3D printed implant of FIG. 4.

FIG. 5 is a flowchart of a process 500 for improving the design of the 3D printed implant of FIG. 4. The process 500 can be performed by the enhancement module 138 of FIG. 1B. One or more other components described herein can also be configured to perform one or more blocks in the process 500. For illustrative purposes, the process 500 is described from the perspective of the enhancement module 138. In some implementations, the blocks performed in the process 500 may be implemented in differing order. Furthermore, the outlined blocks are only provided as examples, and some of the blocks may be optional, combined into fewer operations, or expanded into additional operations without detracting from the essence of the disclosed embodiments.

The process 500 begins with the enhancement module 138 being initiated, at block 501, by the base module 132. The enhancement module 138 extracts, at block 502, the altered 3D image from the image database 146. For example, the enhancement module 138 extracts the altered 3D image that the user created in the process 400 for the design module 136. In some implementations, the enhancement module 138 may extract the original 3D image of the patient's body part that is the area of concern. The enhancement module 138 compares, at block 504, the extracted, altered 3D image to the images stored in the historical database 148. For example, the enhancement module 138 may compare the extracted user-altered 3D image to historical images of healthy patients to further enhance the altered 3D image.

The historical database 148 may be filtered based on the current patient's body part that is an area of concern, such as blood vessel or artery connected to the heart, a disc in the back, etc. The historical database 148 may further be filtered based on measurements of the altered 3D image to ensure that any potential enhancements made would still fit in the required space of the current patient. In some implementations, the historical database 148 may contain data about other patients that have previously had a similar successful procedure performed. The comparison by the enhancement module 138 may provide data about historical patients that would provide an enhancement to the current patient's altered 3D image. For example, if the current patient requires a new blood vessel or artery or stent, the enhancement model 138 can compare the 3D image to historic patient data to provide results of blood vessels, arteries, or stents that allow increased blood flow and are structurally sound that would benefit the current patient, such as an improved pathway or route of the blood vessel that would still maintain the spatial limitations of the previous blood vessel. Another example would be if the patient requires an artificial disc, the enhancement model 138 can perform a comparison of data to provide filtered results from the historical database 148 that includes healthy patients with discs that would be able to fit in an area of concern of the current patient who requires a fix to their damaged disc. The user could view the results to enhance the altered 3D image to further improve strength, structure, flexibility, etc. of an artificial disc that can be 3D printed and inserted into the patient's body at the area of concern.

The enhancement module 138 determines, at block 506, one or more recommendations based on the filtered results from the historical database 148. For example, the enhancement module 138 may determine recommendations based on a comparison of the altered 3D image and the filtered data stored in the historical database 148. The recommendation may be based on a closest match between the altered 3D image and a replacement object from a historically healthy patient, a patient that has previously had a similar procedure, etc. The user may use the recommendation as an example to enhance the altered 3D image. The recommendation may be based on a variety of factors, such as a size that is available inside the current patient to receive the replacement object. Moreover, multiple recommendations can be provided by the enhancement module 138.

In some implementations, the enhancement module 138 can generate a recommendation based on using an algorithm that scores results from a comparison of the altered 3D image to the filtered results from the database 148. The algorithm can use spatial limits of the current patient's body, measurements of the replacement object, performance (e.g., expected and/or actual) of the object, a success rate of the object, etc., to determine the score for each recommendation. Recommendations having a threshold score value can be provided to the user in the CAD GUI 150. Sometimes, a recommendation having a highest score value can be provided to the user. Sometimes, all the recommendations with their assigned score values can be provided to the user in the CAD GUI 150.

A recommendation can be assigned a high score (e.g., a score above some threshold value) if the replacement object can fit exactly within a same space of the patient's body as a previous object, organ, or tissue that will be replaced. The recommendation may also be assigned the high score if, for example, the replacement object is of similar size as the previous object (or within some threshold size range as the previous object), improves functionality of the previous object, and/or provides limited/expected future issues for the patient. As an illustrative example, if the patient is having a blood vessel replaced, a highly scored blood vessel recommendation can include a replacement blood vessel that can be located in a previous location of the damaged blood vessel, having a similar length, width, and diameter as the previous blood vessel, providing improved blood flow, and having been successful for previous patients or otherwise has not been a cause of concern in the future for previous patients.

As another example, if the patient is having a disc replacement, a highly scored recommendation may include an artificial disc that can fit in a same location as the damaged disc, have similar measurements as the damaged disc, provide increased range of motion for the vertebrae of the patient to allow more flexibility, and/or is structurally strong to endure weight and stress of the current patient's body type. Criteria used for scoring each recommendation can vary based on a type of object to be printed and inserted into the patient's body, as well as other information about the health of the patient.

In some implementations, the recommendations may include a 3D image allowing the user to view various aspects of the recommended object. For example, the recommendations may include a series of medical images, such as MRIs, CT scans, x-rays, PET, ultrasounds, etc., allowing the user to view any of the medical images as part of the recommendation. Accordingly, the enhancement module 138 displays, at block 508, the extracted altered 3D image from the image database 146 and the image recommendations from the historical database 148 at the CAD GUI 150. For example, the enhancement module 138 displays the altered 3D image and the recommendations from the historical database 148 to allow the user to further enhance the altered 3D image.

The user may visually compare the information presented at the CAD GUI 150 to identify additional ways to enhance the altered 3D image. For example, the user can review and implement any of the recommendations to enhance the altered 3D image and optimize design and installation of a 3D printed object to improve the patient's condition. Sometimes, the enhancement module 138 may highlight or otherwise provide graphical indications notifying the user about differences between the altered 3D image and the recommendations to allow the user to focus on areas that may be improved upon or otherwise enhanced. In some implementations, the user may select to use the recommendation as the enhanced 3D image without making alterations to the previously altered 3D image.

Accordingly, the user can enhance, at block 510, the extracted altered 3D image using the recommended images from the historical database 148. For example, the user may visually compare the 3D images to identify additional ways to enhance the altered 3D image. The user may select to use a recommendation as the enhanced 3D image without making alterations to the previously altered 3D image. As part of the enhancement process, the enhancement module 138 may modify a virtual representation of a physical 3D apparatus for effecting alterations to the patient's physiology, such as a customized stent, blood vessel graft, artificial disc, etc.

The enhancement module 138 stores, at block 512, the enhanced image in the image database 146. A data file containing the enhanced 3D image may also contain the specifications for the object or apparatus to be 3D printed and inserted into the patient's body, such as measurements, ratio, size, etc. of the object to allow for the 3D image to be printed via the 3D printer 102 to create the object with accurate size and measurements. The enhancement module 138 returns, at block 514, to the base module 132.

Figure 6:
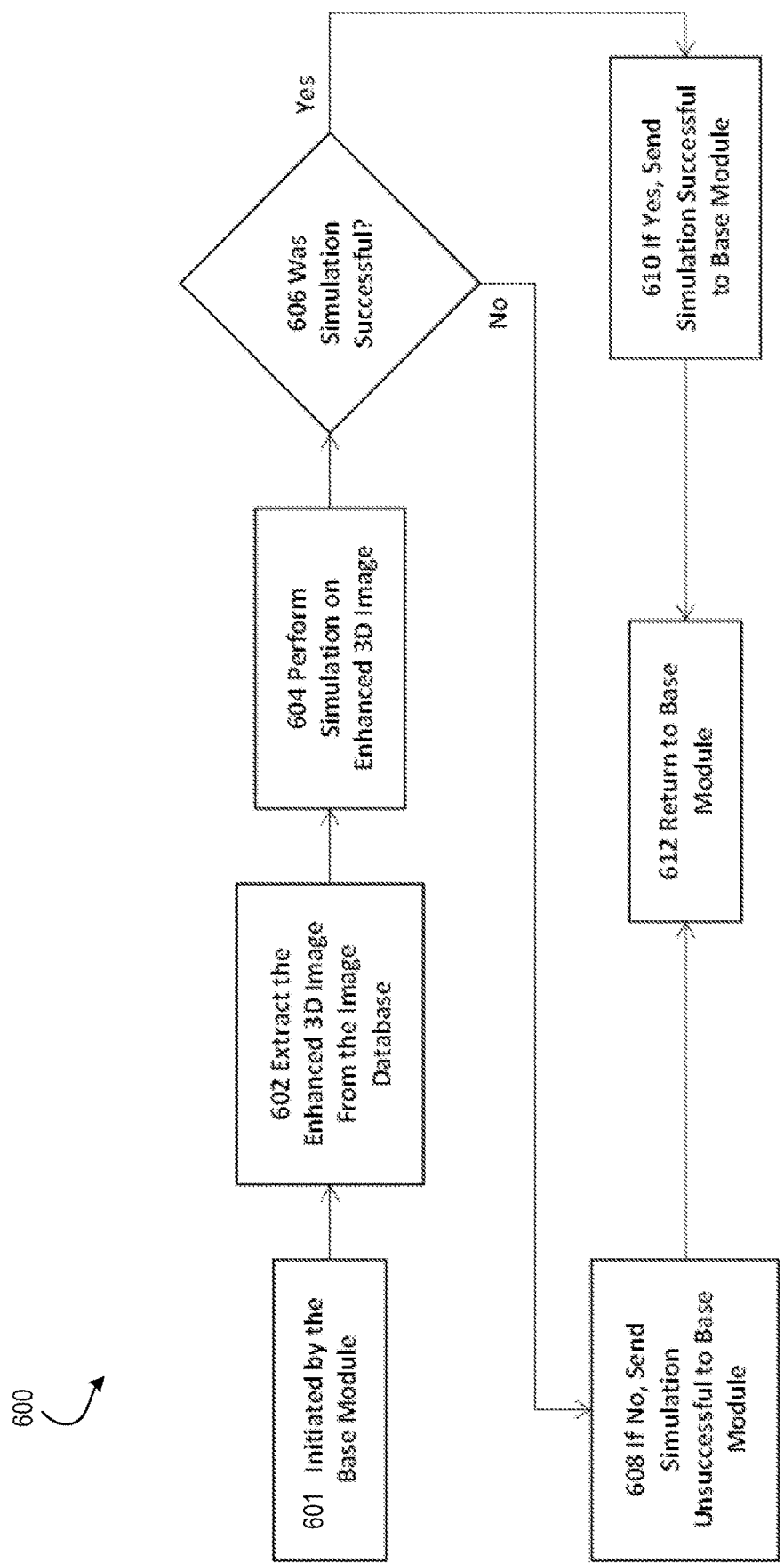
FIG. 6 is a flowchart of a process for simulating design and implantation of a 3D printed implant in a patient's body.

FIG. 6 is a flowchart of a process 600 for simulating design and implantation of a 3D printed implant in a patient's body. The process 600 can be performed by the simulation module 140 of FIG. 1B. One or more other components described herein can also be configured to perform one or more blocks in the process 600. For illustrative purposes, the process 600 is described from the perspective of the simulation module 140. In some implementations, the blocks performed in the process 600 may be implemented in differing order. Furthermore, the outlined blocks are only provided as examples, and some of the blocks may be optional, combined into fewer operations, or expanded into additional operations without detracting from the essence of the disclosed embodiments.

The process 600 begins with the simulation module 140 being initiated, at block 601, by the base module 132. The simulation module 140 extracts, at block 602, the enhanced 3D image from the image database 146. The enhanced 3D image may include additional data, such as specifications for a replacement object, apparatus, and/or structure to be 3D printed and then inserted into tan area of concern in the patient's body.

The simulation module 140 performs, at block 604, a simulation on the extracted enhanced 3D image. The simulation module 140 performs the simulation to determine, if the 3D image is printed by the 3D printer 102, whether the object would be successful or unsuccessful. The simulation may be a computer program that analyzes a success rate of the 3D image being printed and implanted or transplanted into the current patient's area of concern. Such programs, often known as slicers, can be used for simulations. Additionally, finite point analysis and other such simulations may be used. For example, the simulation module 140 may determine if the 3D image, when printed into an actual 3D object, would fit into a space available inside the patient's body, whether measurements of the 3D printed object would be similar to or within some threshold as the previous object or organ inside the patient, whether the 3D printed object would fit or interact with other body parts in close proximity, an expected performance of the 3D printed object, and/or potential future conditions that may arise from printing and inserting the 3D printed object into the patient's body. As some additional examples, the simulation module 140 may determine if measurements of the 3D printed object would physically fit in the space available that is left by the previous object inside the patient's body, determine if the size of the newly 3D printed object is similar in relation to the previous object, determine if the 3D printed object would interfere, damage, or otherwise disrupt the function of objects surrounding it, determine if the 3D printed object would improve functionality over the previous object, and/or determine if the 3D object would require additional procedures and/or potentially fail in the future.

As an illustrative example, if the 3D printed object is a blood vessel or artery, the simulation module 140 can simulate printing and insertion of the 3D printed object into the patient to determine whether that 3D printed blood vessel or artery would fit into the previous blood vessel or artery location inside the patient's body, whether the 3D printed blood vessel or artery would connect successfully to blood vessels, arteries, heart, etc. around it, whether the 3D printed blood vessel or artery would successfully improve blood flow, and/or whether the 3D printed blood vessel or artery has the potential of being damaged, such as due to constant flow of blood, movements made by the patient, structure of the blood vessel or artery being able to be maintained, etc. The simulation module 140 can then score results from running the simulation(s) to determine whether the 3D printed object should be printed and inserted into the patient. A score value can be assigned based on how well or whether any of the above determinations are satisfied by the 3D printed object.

As another illustrative example, if the 3D printed object is an artificial disc, the simulation module 140 can determine if the artificial disc would fit in the location of the damaged disc, how the artificial disc would interact or function in between the two vertebrae and nerves, and/or if the disc would provide additional flexibility and less pain for the patient or if the disc would limit movements of the patient or result in discomfort. Based on how the 3D printed object performs in the simulation, the simulation module 140 can score the 3D printed object. A high score (e.g., above a threshold value) can indicate that the 3D printed object has been optimized and can successfully be printed and inserted into the patient to provide the patient with health benefits/improvements. A low score (e.g., below the threshold value) can indicate that the 3D printed object may not be optimized and therefore should be further enhanced and/or altered before being printed and inserted into the patient.

As described herein, various different objects can be 3D printed using the disclosed techniques. For example, the object can be a flange connection customized to bone or surrounding tissue to increase an area of an interface between an implant and bone tissue and durability of that connection. The flange may have an increased surface area including channels to further increase the surface area of the interface and may also feature one or more holes for a screw. Another example may be a custom array of needles dispersed around a network of nerve tissue to provide targeted stimulation, which may be designed to fit the bone or tissues to which the array is affixed to or to the nerves in which it interacts. The array of needles may be capable of selectively providing a stimulus in response to data collected from sensors 110 monitoring the patient or may execute a sequence of stimuli to provide a therapeutic effect.

The results of the simulation can provide either a successful or unsuccessful result, which would be sent to the base module 132. If unsuccessful, the process 600 can return an indication to the base module 132 (blocks 608 and 612), which can trigger the design module 134 to allow the user to improve the design and further enhance the 3D image, as described in reference to FIGS. 4-5. Whenever the 3D image is improved and/or enhanced, the simulation can be run again through the process 600.

If the simulation is successful, an indication of success can be transmitted to the base module 132 (blocks 610 and 612). The base module 132 can then perform operations to cause the 3D image to be printed. A successful result would, therefore, represent that a modification to the patient, such as via insertion of the 3D printed object, that meets requirements outlined by the user, can be successfully performed to improve the patient's health condition. For example, if the 3D object is a stent, the stent may be required to withstand a pressure of 300 mmHg. If, when simulated, the 3D printed stent may not be able to withstand that pressure, then the simulation is unsuccessful. If the 3D object is an artificial disc, the object may be required to function under a load of 1000 kg. If the 3D printed artificial disc can sustain at least a load of 1000 kg in the simulation, then the simulation was successful and the artificial disc, as simulated, can be printed and inserted into the patient. Similarly, any 3D object may be required to have a lifecycle of at least 20 years. If a 3D printed object, in simulation, may not last for at least a predetermined threshold amount of time (e.g., 20 years), then the simulation may be unsuccessful and the object design should further be improved/optimized.

Figure 7:
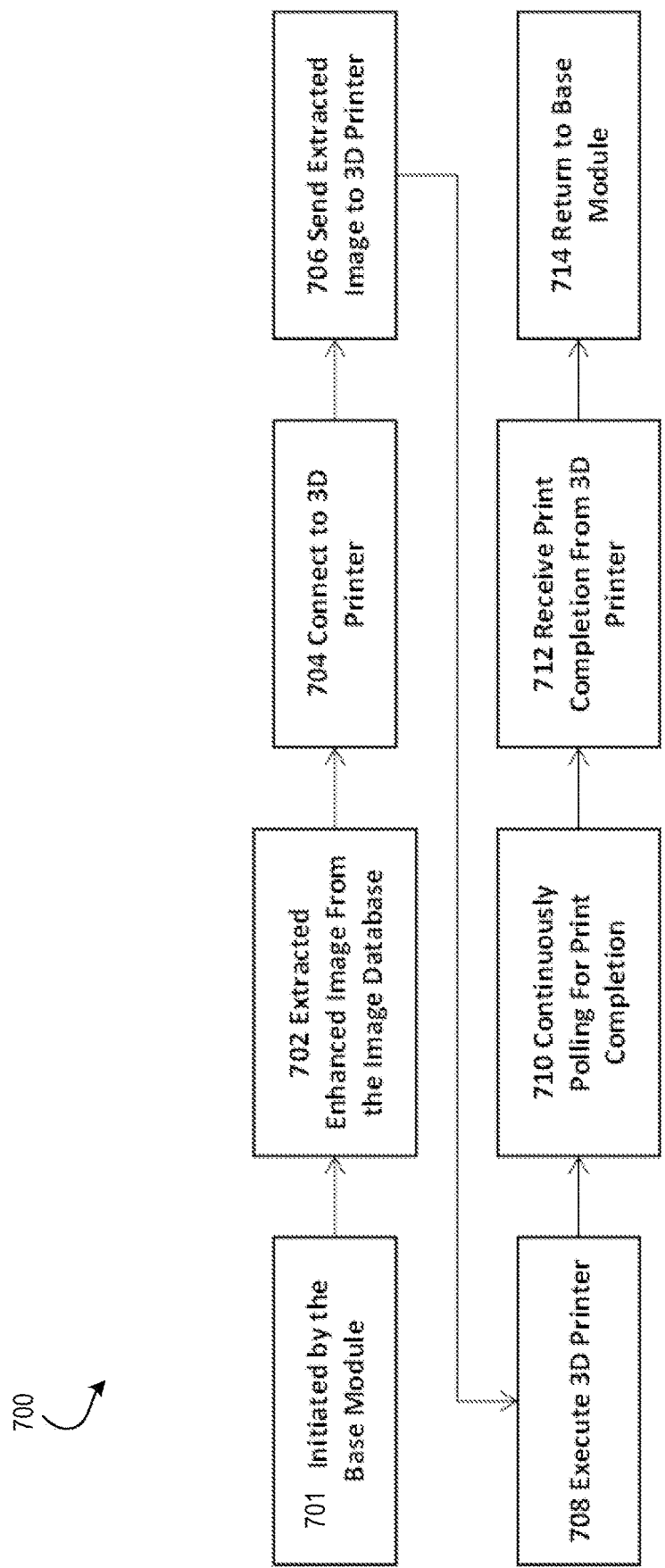
FIG. 7 is a flowchart of a process for 3D printing a 3D printed implant using the disclosed techniques.

FIG. 7 is a flowchart of a process 700 for 3D printing a 3D printed implant using the disclosed techniques. The process 700 can be performed by the print module 142 of FIG. 1B. One or more other components described herein can also be configured to perform one or more blocks in the process 700. For illustrative purposes, the process 700 is described from the perspective of the print module 142. In some implementations, the blocks performed in the process 700 may be implemented in differing order. Furthermore, the outlined blocks are only provided as examples, and some of the blocks may be optional, combined into fewer operations, or expanded into additional operations without detracting from the essence of the disclosed embodiments.

The process 700 begins with the print module 142 being initiated, at block 701, by the base module 132. The print module 142 extracts, at block 702, the enhanced image from the image database 146. For example, the print module 142 retrieves the enhanced 3D image that has successfully passed the simulation in the process 600. The enhanced 3D image can include a 3D model to be printed using the 3D printer 102 as well as any additional data and/or instructions needed to operate the 3D printer 102 to accurately print an object represented by the 3D model.

The print module 142 can connect, at block 704, to the 3D printer 102. For example, the print module 142 communicates to the 3D printer 102 through the cloud 128. The print module 142 sends, at block 706, the enhanced image to the 3D printer 102. For example, the print module 142 sends a data file including the enhanced 3D image. The data file may also contain exact measurements for the object to be printed, a substrate to be used or types of biomaterials or bio-ink to be used, one or more steps and/or instructions for printing the object, etc.

As an illustrative example, the object can be a stent to be printed out of titanium using a selective laser sintering. This information can be provided, along with printing instructions, via the connection established between the print module 142 and the 3D printer 102. As another example, the object can be an artificial disc made of polylactic-co-glycolic acid. Information about printing the artificial disc with such material can be provided to the 3D printer 102.

The print module 142 executes, at block 708, the 3D printer 102 to print the enhanced 3D image. For example, the print module 142 sends the data file of the 3D object containing the measurements, substrate, and method to be printed to the 3D printer 102. Upon receipt of the data file, the 3D printer 102 can be configured to execute the method and print the object.

3D bioprinting is utilization of 3D printing technologies to assemble multiple cell types or stem cells/growth factors along with other biomaterials in a layer-by-layer fashion to produce bioartificial organs that maximally imitate their natural counterparts. Bioprinting is 3D printing of biological tissue and organs through layering of living cells. For example, 3D bioprinting for fabricating biological constructs involves dispensing cells onto a biocompatible scaffold using a successive layer-by-layer approach to generate tissue-like 3D structures. Some of the methods used for 3D bioprinting of cells can include photolithography, magnetic 3D bioprinting, stereolithography, and direct cell extrusion, all of which may be used by the 3D printer 102. In some implementations, synthetic biocompatible materials may be utilized in addition to or in place of biomaterials.

The print module 142 can continuously poll, at block 710, for a print completion signal from the 3D printer 102. For example, the print module 142 can continuously receive a status of whether the printing is in progress, completed, or reached an error state. Eventually, the print module 142 can receive, at block 712, the print completion signal from the 3D printer 102. The print completion status can notify the user that the print operation has completed and that the object has been 3D printed according to the enhanced 3D image and associated data. In some implementations, the user may be notified through the CAD GUI 150, or the user may control, operate, or track progress of the printing directly at/from the CAD GUI 150. Finally, the print module 142 can return, at block 714, to the base module 132 upon completion of the process 700.

Figure 8:
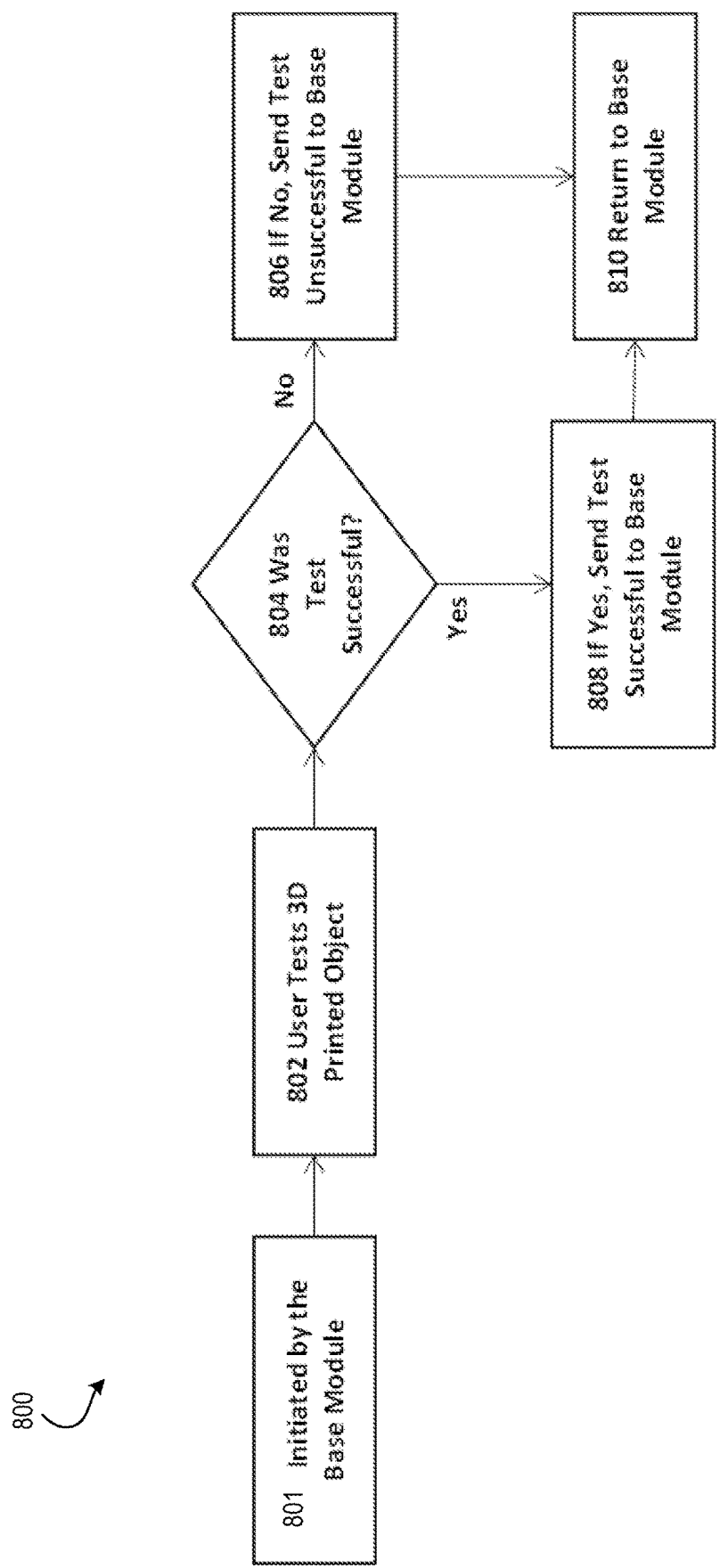
FIG. 8 is a flowchart of a process for testing a 3D printed implant using the disclosed techniques.

FIG. 8 is a flowchart of a process 800 for testing a 3D printed implant using the disclosed techniques. The process 800 can be performed by the test module 144 of FIG. 1B. One or more other components described herein can also be configured to perform one or more blocks in the process 800. For illustrative purposes, the process 800 is described from the perspective of the test module 144. In some implementations, the blocks performed in the process 800 may be implemented in differing order. Furthermore, the outlined blocks are only provided as examples, and some of the blocks may be optional, combined into fewer operations, or expanded into additional operations without detracting from the essence of the disclosed embodiments.

The process 800 begins with the test module 144 being initiated, at block 801, by the base module 132. The user tests, at block 802, the 3D printed object. For example, the user may test the 3D printed object to determine if the object is safe to be used by the patient. The user may perform one or more different tests to determine safety, functionality, and performance of the 3D printed object to ensure that it does not fail or be rejected by the patient. For example, the user can perform one or more tests to check whether a substrate, biomaterial, or bio-ink used for printing the object would cause a current patient to reject the object. To ensure that the 3D printed object was created using the patient's preferred substrate (or a substrate that has been determined to not be rejected by the patient's body), the user may perform a blood type test, a tissue typing test or blood test for human leukocyte antigens (HLA), a crossmatch test, and/or a serology test.

In some implementations, the user may test the functionality and performance of the 3D printed object. For example, for a blood vessel or artery, the user can test a flow of blood through the blood vessel or artery, or for an artificial disc, the user can test an amount of weigh the artificial disc can support and/or a flexibility of the disc.

The test module 144 determines, at step 804, if the test was successful or unsuccessful. For example, the test module 144 may determine if the test was successful or unsuccessful through inputs made by the user at the CAD GUI 150 once the tests are complete. If it is determined that the test was unsuccessful, the test module 144 sends, at block 806, a signal to the base module 132 indicating that the test was unsuccessful. For example, the test may be deemed unsuccessful if the test results were not within acceptable threshold or predetermined levels such as the object being found to be biologically incompatible with the patient, the object being unable to maintain its integrity when subjected to a load test, and/or a pathogen or other contaminant being found on the object. In some embodiments, an unsuccessful test would indicate the implant could be modified by the design module or enhanced by the enhancement module and reprinted until an implant which is successful has been obtained.

If it is determined that the test was successful, the test module 144 sends, at block 808, a signal to the base module 132 indicating that the test was successful. For example, the test may be deemed successful if a threshold quantity of the tests (or all the tests) returned favorable results within expected or predetermined ranges, such as bearing a load without deforming, being free of contaminants, etc. If the test is successful, then the 3D printed object is ready to be inserted into the patient's body. The test module 144 can then return, at block 810, to the base module 132.

FIG. 9 illustrates example image data 900 that can be used to design and optimize a 3D printed implant. As described above, the patient image data 900 can be stored in the image database 146 after the data 900 is collected by the imaging module 134. The patient image data 900 can include, for each patient, a patient ID, regions of the patient's body that the image(s) capture, type(s) of image(s) captured, such as an MM, CT scan, X-ray, ultrasound, PET, etc., a 3D image data file, an altered 3D image data file, and/or an enhanced 3D image data file. One or more additional, fewer, or other data may also be stored in association with each patient for use in performing the disclosed techniques.

FIG. 10 illustrates example historic patient data 1000 that can be used to design and optimize a 3D printed implant. As described above, the historic patient data 1000 can be stored in the historical database 148. The data 1000 may include historical patient's medical imaging data for a variety of patients. The data 1000 can correspond to healthy patient's and may be used as one or more recommendations for enhancing a current patient's 3D printed object, such as a blood vessel, tissue, organ, cartilage, bone, etc. The data 1000 can be retrieved and used by the enhancement module 138 to enhance the altered 3D image created by the user and/or provide recommendations for enhancing the altered 3D image. The data 1000 can include, for example and for each patient of record, patient IDs, regions of the patient's body that the image(s) capture, and/or type(s) of image(s) captured, such as an MM, CT scan, X-ray, ultrasound, PET, etc.

In some embodiments, data from various patients can be combined to determine recommendations tailored to a particular patient's condition. Several statistical methods can be employed to identify patient parameters that may impact implant design parameters: Correlation analysis: This method measures the degree of association between patient parameters and implant design factors. It can help identify the strength and direction of the relationship between variables (e.g., patient height and implant size); Regression analysis: Regression techniques model the relationship between a dependent variable (e.g., implant performance) and one or more independent variables (e.g., patient parameters). This can be used to predict implant design parameters based on specific patient conditions; Cluster analysis: This technique groups patients with similar characteristics, allowing for the identification of common trends or patterns in implant design parameters that are effective for specific patient profiles; Principal component analysis (PCA): PCA reduces the dimensionality of the data by identifying a smaller set of uncorrelated variables (principal components) that capture the most significant patterns in the original data. This can help isolate the most influential patient parameters affecting implant design; Machine learning algorithms: Techniques such as decision trees, random forests, or neural networks can be used to identify complex relationships between patient parameters and implant design factors, improving the accuracy of personalized recommendations; Bayesian inference: This method updates the probability of a hypothesis as more evidence or patient data becomes available, allowing for more accurate predictions and recommendations based on the accumulated data. By using these techniques, practitioners can combine data from various patients to derive personalized implant design recommendations that account for the specific patient's condition and unique characteristics.

Several imaging modalities and computer vision techniques may be used to optimize implants for a particular patient based on historical patient data. For example, magnetic Resonance Imaging (MM): Mill uses magnetic fields and radio waves to generate detailed images of the internal structures of the body. It can help visualize soft tissues, cartilage, and bone for joint implant planning; Computed Tomography (CT) scans: CT scans use X-rays to generate cross-sectional images of the body, providing detailed information about bone structure and density, which is essential for implant planning and design; X-ray imaging: X-ray images provide a two-dimensional view of the body's internal structures, particularly the skeletal system, which can be useful for determining implant parameters such as size, shape, and alignment; Ultrasound imaging: Ultrasound uses high-frequency sound waves to create real-time images of the body's internal structures. It can be useful for visualizing soft tissues and guiding implant placement; Optical coherence tomography (OCT): OCT is a non-invasive imaging technique that uses light to capture high-resolution images of biological tissue. It can be used for assessing the surface and subsurface structures in certain implant applications. To process and analyze these medical images, various computer vision techniques can be employed, for example: Image segmentation: This technique divides an image into distinct regions or objects, allowing the algorithm to isolate and analyze the relevant anatomical structures for implant planning; Feature extraction: Feature extraction techniques identify and quantify specific characteristics in the images, such as shape, texture, or intensity, which can be used as input for the algorithm to determine implant parameters; Deep learning algorithms: Convolutional neural networks (CNNs) and other deep learning architectures can be trained to automatically detect and classify anatomical structures in medical images, providing valuable information for implant parameter identification; Registration and fusion: These techniques align and combine information from different imaging modalities or multiple images of the same patient, enabling a comprehensive assessment of the relevant anatomical structures for implant planning.

Moreover, advanced surgical systems, as described herein, can include many different types of equipment to monitor and anesthetize the patient, assist the surgeon in performing surgical tasks, and maintain the environment of the operating room. Non-limiting examples of surgical equipment that may be used or improved by the present invention are provided for reference.

Vital signs monitor refers to medical diagnostic instruments and in particular to a portable, battery powered, multi-parametric, vital signs monitoring device that can be used for both ambulatory and transport applications as well as bedside monitoring. These devices can be used with an isolated data link to an interconnected portable computer allowing snapshot and trended data from the monitoring device to be printed automatically and also allowing default configuration settings to be downloaded to the monitoring device. The monitoring device is capable of use as a stand-alone unit as well as part of a bi-directional wireless communications network that includes at least one remote monitoring station. A number of vital signs monitoring devices are known that are capable of measuring multiple physiologic parameters of a patient wherein various sensor output signals are transmitted either wirelessly or by means of a wired connection to at least one remote site, such as a central monitoring station. A vital signs monitor can be integrated into the embodiments in a variety of manners.

Heart rate monitor refers to the sensor(s) and/or sensor system(s) that can be applied in the context of monitoring heart rates. Embodiments are intended to measure, directly or indirectly, any physiological condition from which any relevant aspect of heart rate can be gleaned. For example, some of the embodiments measure different or overlapping physiological conditions to measure the same aspect of heart rate. Alternatively, some embodiments measure the same, different, or overlapping physiological conditions to measure different aspects of heart rate, i.e., number of beats, strength of beats, regularity of beats, beat anomalies, etc. A heart rate monitor can be integrated into the embodiments in a variety of manners.

Pulse oximeter or SpO2 Monitor refers to a plethysmograph or any instrument that measures variations in the size of an organ or body part on the basis of the amount of blood passing through or present in the part. An oximeter is a type of plethysmograph that determines the oxygen saturation of the blood. One common type of oximeter is a pulse oximeter. A pulse oximeter is a medical device that indirectly measures the oxygen saturation of a patient's blood (as opposed to measuring oxygen saturation directly through a blood sample) and changes in blood volume in the skin. A pulse oximeter may include a light sensor that is placed at a site on a patient, usually a fingertip, toe, forehead, or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation. A pulse oximeter can be integrated into the embodiments in a variety of manners.

End Tidal CO2 monitor or capnography monitor refers to an instrument which is used for measurement of level of carbon dioxide (referred to as end tidal carbon dioxide, ETCO2) that is released at the end of an exhaled breath. End tidal CO2 monitor or capnography monitor is widely used in anesthesia and intensive care. ETCO2 can be calculated by plotting expiratory CO2 with time. Further, ETCO2 monitor plays a very crucial role for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The instrument can be configured as side stream (diverting) or mainstream (non-diverting). Diverting device transports, a portion of a patient's respired gases from the sampling site to the sensor while non-diverting device does not transport gas away. Also, measurement by the instrument is based on the absorption of infrared light by carbon dioxide, where exhaled gas passes through a sampling chamber containing an infrared light source and photodetector on both sides. Based on the amount of infrared light reaching the photodetector, the amount of carbon dioxide present in the gas can be calculated. An ETCO2 monitor or capnography monitor can be integrated into the embodiments in a variety of manners.

Blood pressure monitor refers to any instrument that measures blood pressure, particularly in arteries. Blood pressure monitors use a non-invasive technique (by external cuff application) or an invasive technique (by a cannula needle inserted in artery, used in operating theatre) for measurement, with non-invasive measurement being widely used. The non-invasive method (referred to as sphygmomanometer further) works by measurement of force exerted against arterial walls during ventricular systole (i.e., systolic blood pressure, occurs when heart beats and pushes blood through the arteries) and ventricular diastole (i.e., diastolic blood pressure, occurs when heart rests and is filling with blood) thereby measuring systole and diastole, respectively. It can be of three types automatic/digital, manual (aneroid-dial), and manual (mercury-column). The sphygmomanometer may include a bladder, a cuff, a pressure meter, a stethoscope, a valve, and a bulb. The cuff then inflates until it fits tightly around your arm, cutting off your blood flow, and then the valve opens to deflate it. It operates by inflating a cuff tightly around the arm, as the cuff reaches the systolic pressure, blood begins to flow around your artery, and creating a vibration which is detected by the meter, which records your systolic pressure. This systolic pressure is recorded. The techniques used for measurement may be: auscultatory or oscillometric. A blood pressure monitor can be integrated into the embodiments in a variety of manners.

Body temperature monitor refers to any instrument which is used for measurement of body temperature. The instrument can measure the temperature invasively or non-invasively by placement of sensor into organs such as bladder, rectum, esophagus, tympanum, esophagus, etc., and mouth, rectum, armpit, etc., respectively. The sensors are of two types: contact and non-contact. It can be measured in two forms: core temperature and peripheral temperature. Temperature measurement can be done by these sensing technologies: thermocouples, resistive temperature devices (RTDs, thermistors), infrared radiators, bimetallic devices, liquid expansion devices, molecular change-of-state, and silicon diodes. A thermometer which is a commonly used instrument for the measurement of temperature consists of a temperature sensing element (e.g., temperature sensor) and a means for converting to a numerical value. A blood temperature monitor can be integrated into the embodiments in a variety of manners.

Respiration rate or breathing rate is the rate at which breathing occurs and is measured by a number of breaths a person takes per minute. The rate is usually measured when a person is at rest and simply involves counting the number of breaths for one minute by counting how many times the chest rises. Normal respiration rates for an adult person at rest are in the range: 12 to 16 breaths per minute. A variation can be an indication of an abnormality/medical condition or a patient's demographic parameters. Hypoxia is a condition with low levels of oxygen in the cells and hypercapnia is a condition in which high levels of carbon dioxide in the bloodstream. Pulmonary disorders, asthma, anxiety, pneumonia, heart diseases, dehydration, drug overdose are some of the abnormal conditions which can bring a change to the respiration rate, thereby increasing or reducing the respiration rate from normal levels. Respiratory rate can be integrated into the embodiments in a variety of manners.

An electrocardiogram abbreviated as EKG or ECG refers to a representation of the electrical activity of the heart (graphical trace of voltage versus time) which is done by placement of electrodes on skin/body surface. The electrodes capture the electrical impulse which travels through the heart causing systole and diastole or the pumping of the heart. This impulse gives a lot of information related to the normal functioning of the heart and the production of impulses. A change may occur due to medical conditions such as arrhythmias (tachycardia where the heart rate becomes faster and bradycardia where the heart rate becomes slower), coronary heart disease, heart attacks, cardiomyopathy. The instrument used for the measurement of the electrocardiogram is called an electrocardiograph which measures the electrical impulses by the placement of electrodes on the surface of the body and represents the ECG by a PQRST waveform. PQRST wave is read as: P wave which represents the depolarization of the left and right atrium and corresponding to atrial contraction, QRS complex indicates ventricular depolarization and represents the electrical impulse as it spreads through the ventricles; T wave indicates ventricular repolarization and follows the QRS complex. An electrocardiogram can be integrated into the embodiments in a variety of manners.

Neuromonitoring also called Intraoperative neurophysiological monitoring (abbreviated as IONM) refers to an assessment of functions and changes in the brain, brainstem, spinal cord, cranial nerves, and peripheral nerves during a surgical procedure on these organs. It includes both continuous monitoring of neural tissue as well as the localization of vital neural structures. IONM measures changes in these organs which are indicative of irreversible damage, injuries in the organs, aiming at reducing the risk of neurological deficits after operations involving the nervous system. This has also been found to be effective in localization of anatomical structures, including peripheral nerves and sensorimotor cortex, which help in guiding the surgeon during dissection. Electrophysiological modalities which are employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires specific anesthesia techniques to avoid interference and signal alteration due to anesthesia. Neuromonitoring can be integrated into the embodiments in a variety of manners.

Motor evoked potential abbreviated as MEP refers to electrical signals which are recorded from descending motor pathways or muscles following stimulation of motor pathways within the brain. MEP may be calculated by measurement of the action potential which is elicited by non-invasive stimulation of the motor cortex through the scalp. MEP is a widely used technique for intraoperative monitoring and neurophysiological testing of the motor pathways specifically during spinal procedures. The technique of monitoring for measurement of MEP can be defined based on some of the parameters like a site of stimulation (motor cortex or spinal cord), method of stimulation (electrical potential or magnetic field), and site of recording (spinal cord or peripheral mixed nerve and muscle). The target site may be stimulated by the use of electrical or magnetic means. MEP can be integrated into the embodiments in a variety of manners.

Somatosensory evoked potential abbreviated as SSEP, or SEP refers to the electrical signals which are elicited by the brain and the spinal cord in response to sensory stimulus or touch. SSEP is one of the most frequently used techniques for intraoperative neurophysiological monitoring in spinal surgeries. The method proves to be very reliable which allows for continuous monitoring during a surgical procedure. However, accuracy may be a concern at times in measurement. The sensor stimulus which is commonly given to the organs may be auditory, visual, or somatosensory SEPs and applied on the skin, peripheral nerves of the upper limb, lower limb, or scalp. The stimulation technique may be mechanical (widely used), or electrical (found to give larger and more robust responses), intraoperative spinal monitoring modality. Somatosensory evoked potential can be integrated into the embodiments in a variety of manners.

Electromyography abbreviated as EMG refers to the evaluation and recording of electrical signals or electrical activity of the skeletal muscles. Electromyography instrument or electromyograph or electromyogram, the instrument for the measurement of the EMG activity works on a technique used for a recording of electrical activity produced by skeletal muscles and evaluation of the functional integrity of individual nerves. The nerves which are monitored by the EMG instrument may be intracranial, spinal, or peripheral nerves. The electrodes which may be used for the acquisition of signals may be invasive and non-invasive electrodes. The technique used for measurement may be spontaneous or triggered. Spontaneous EMG refers to the recording of myoelectric signals during surgical manipulation such as compression, stretching, or pulling of nerves produces; and does not perform external stimulation. Spontaneous EMG may be recorded by the insertion of a needle electrode. Triggered EMG refers to the recording of myoelectric signals during stimulation of target site such as pedicle screw with incremental current intensities. Electromyography can be integrated into the embodiments in a variety of manners.

Electroencephalography abbreviated as EEG refers to the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp where each pair of electrodes transmit a signal to one or more recording channels. It is one of the oldest and most commonly utilized modalities for intraoperative neurophysiological monitoring and assessing cortical perfusion and oxygenation during a variety of vascular, cardiac, and neurosurgical procedures. The waves produced by EEG are alpha, beta, theta, and delta. Electroencephalography can be integrated into the embodiments in a variety of manners.

Medical visualization systems refer to visualization systems that are used for visualization and analysis of objects (preferably three-dimensional (3D) objects). Medical visualization systems include the selection of points at surfaces, selection of a region of interest, selection of objects. Medical visualization systems may be used for applications diagnosis, treatment planning, intraoperative support, documentation, educational purpose. Medical visualization systems may consist of microscopes, endoscopes/arthroscopes/laparoscopes, fiber optics, surgical lights, high-definition monitors, operating room cameras, etc. 3D visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times. Medical visualization systems can be integrated into the embodiments in a variety of manners.

A microscope refers to an instrument that is used for viewing samples & objects that cannot be seen with an unaided eye. A microscope may have components eyepiece, objective lenses, adjustment knobs, stage, illuminator, condenser, diaphragm. A microscope works by manipulating how light enters the eye using a convex lens, where both sides of the lens are curved outwards. When light reflects off of an object being viewed under the microscope and passes through the lens, it bends towards the eye. This makes the object look bigger than it is. A microscope may be of types compound (light illuminated and the image seen with the microscope is two dimensional), dissection or stereoscope (light illuminated and image seen with the microscope is three dimensional), confocal (laser-illuminated and image seen with the microscope on a digital computer screen), scanning electron abbreviated as SEM (electron illuminated and image seen with the microscope in black and white), transmission electron microscope abbreviated as TEM (electron illuminated and image seen with the microscope is the high magnification and high resolution). A microscope can be integrated into the embodiments in a variety of manners.

Endoscopes or arthroscopes or laparoscopes refer to minimally invasive surgical techniques where procedures are performed by performing minimal incision in the body. An endoscope refers to an instrument to visualize, diagnose, and treat problems inside hollow organs where the instrument is inserted through natural body openings such as the mouth or anus. An endoscope may perform a procedure as follows: scope with a tiny camera attached to a long, thin tube is inserted. The doctor moves it through a body passageway or opening to see inside an organ. It can be used for diagnosis and surgery (such as for removing polyps from the colon). Arthroscope refers to an instrument to visualize, diagnose, and treat problems inside a joint by a TV camera inserted through small portals/incisions and perform procedures on cartilage, ligaments, tendons, etc. An endoscope may perform the procedure as follows: a surgeon makes a small incision in a patient's skin and inserts a pencil-sized instrument with a small lens and lighting system to magnify the target site (joint) and viewing of the interior of the joint by means of a miniature television camera and performing procedure. Endoscope refers to an instrument to visualize, diagnose, and treat problems inside soft organs like the abdomen and pelvis by a TV camera inserted through small portals/incisions and perform procedures. Endoscopes/arthroscopes/laparoscopes or minimally invasive surgery techniques can be integrated into the embodiments in a variety of manners.

Fiber optics refers to flexible, transparent fiber made by drawing glass (silica) or plastic to a diameter slightly thicker than that of a human hair. Fiber optics are arranged in bundles called optical cables and used to transmit light signals over long distances. Fiber optics are used most often as a means to transmit light between the two ends of the fiber and find wide usage in the medical field. Traditional surgery requires sizable and invasive incisions to expose internal organs and operate on affected areas and with fiber optics much smaller surgical incisions can be performed. Fiber optics contain components core, cladding, buffer coating. Fiber optics may be inserted in hypodermic needles and catheters, endoscope, operation theatres, ophthalmology, dentistry tools. Fiber optics sensors comprise a light source, optical fiber, external transducer, and photodetector. Fiber-optic sensors may be intrinsic or extrinsic. Fiber optics sensors may be categorized into four types physical, imaging, chemical, and biological. Fiber optics can be integrated into the embodiments in a variety of manners.

Surgical lights also referred to as operating light refers to an instrument that performs illumination of a local area or cavity of the patient. Surgical lights play an important role in illumination before, during, and after a medical procedure. Surgical lights may be categorized by lamp type as conventional (incandescent) and LED (light-emitting diode). Surgical lights may be categorized by mounting configuration as ceiling-mounted, wall-mounted, or floor stand. Surgical lights may be categorized by type as tungsten, quartz, and/or xenon halogens and light-emitting diodes (LEDs). Surgical lights include sterilizable handles which allow the surgeon to adjust light positions. Some important factors affecting surgical lights may be illumination, shadow management (cast shadows and contour shadows), the volume of light, heat management, fail-safe surgical lighting. Surgical lights can be integrated into the embodiments in a variety of manners.

High-definition monitors refer to a display in which a clearer picture than possible with low-definition, low-resolution screens. High-definition monitors have a higher density of pixels per inch than past standard TV screens. Resolution for high-definition monitors may be 1280×720 pixels or more. Full HD—1920×1080, Quad HD—2560×1440, 4K—3840×2160, 8K—7680×4320 pixels. High-definition monitor may operate in progressive or interlaced scanning mode. High definition monitors used in medical applications may offer the following advantages improved visibility and allows for precise and safe surgery, rich color reproduction and provides suitable colors for each clinical discipline, better visibility, and operability with a large screen and electronic zoom, higher image quality in low light conditions, high contrast at high spatial frequencies, twice as sensitive as conventional sensors, easier determination of tissue boundaries (fat, nerves, vessels, etc.), better visualization of blood vessels and lesions. High-definition monitors can be integrated into the embodiments in a variety of manners.

Operating room cameras refer to cameras that collect images from 360 degrees, and sensors that monitor both the operating room and people in it. Operating room cameras consist of cameras that are equipped in system and perform recording to give a bird's-eye view to the surgical team. Some cameras are on devices that surgeons insert through small incisions or orifices to see what they are doing during minimally invasive surgery. Operating room cameras may perform recording for this purpose: educational purposes: example—to broadcast a live feed of a surgical demonstration to a remote audience, to collect authentic footage for edited, instructional videos on a surgical technique or procedure; to facilitate video enhanced debriefing and coaching, or to formally assess surgical skills. Operating room cameras can be integrated into the embodiments in a variety of manners.

Surgical tower refers to an instrument used for performing minimally invasive surgery or surgery which is performed by creating small incisions in the body, therefore they are also referred to as minimally invasive devices or minimally invasive access devices. The procedure of performing minimally invasive surgery may be referred to as minimally invasive procedure or minimally invasive surgery, abbreviated as MIS. MIS is a safe, less invasive, and precise surgical procedure. Some of the advantages offered by surgical towers may be small incisions, less pain, low risk of infection, short hospital stays, quick recovery time, less scarring, and reduced blood loss. Some medical procedures where surgical towers are useful and are widely used may be lung procedures, gynecological, head and neck, heart, and urological conditions. MIS may be robotic or non-robotic/endoscopic. MIS may include the following: endoscopic, laparoscopic, arthroscopic, natural orifice intraluminal, and natural orifice transluminal procedures. A surgical tower access device may be designed as an outer sleeve and an inner sleeve that telescoping or slidably engages with one another. When a telescope is used to operate on the abdomen, the procedure is called laparoscopy. Surgical towers typically include access to a variety of surgical tools, such as, for example, electrocautery, radiofrequency, lasers, sensors, etc. A surgical tower can be integrated into the embodiments in a variety of manners.

Electrocautery refers to an instrument that is used for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision an electrocautery instrument may be used. For example: after removing part of the liver for removal of tumor etc., blood vessels in the liver must be sealed individually. An electrocautery instrument may be used for sealing living tissue such as arteries, veins, lymph nodes, nerves, fats, ligaments, and other soft tissue structures. It may be used in applications surgery, tumor removal, nasal treatment, wart removal. Electrocautery may operate in modes two monopolar or bipolar. The electrocautery instrument may consist of a generator, a handpiece, and one or more electrodes. Electrocautery can be integrated into the embodiments in a variety of manners.

Radiofrequency (RF) is used in association with minimally invasive surgery devices. The radiofrequency (RF) may be used for the treatment of skin by delivering it to the skin through a minimally invasive tool (fine needles) which does not require skin excision. The RF may be used for real-time tracking of minimally invasive surgery devices such as laparoscopic instruments. The RF may provide radiofrequency ablation to a patient suffering from atrial fibrillation through smaller incisions made between the ribs. The RF may be used to perform an endoscopic surgery on the body such as the spine by delivery of RF energy. Radiofrequency can be integrated into the embodiments in a variety of manners.

Laser is used in association with minimally invasive surgery devices. The laser may be used in minimally invasive surgeries with an endoscope. The laser is attached to the distal end of the endoscope and steers the laser at high speed by producing higher incision quality than existing surgical tools and minimizing damage to surrounding tissue. Laser may be used to perform minimally invasive surgeries using an endoscope, laparoscope in the lower and upper gastrointestinal tract, eye, nose, and throat. Lasers are used in minimally invasive surgery to ablate soft tissues, such as a herniated spinal disc bulge. Laser can be integrated into the embodiments in a variety of manners.

Sensors are used in association with minimally invasive surgery devices. The sensor may be used in minimally invasive surgeries for tactile sensing of tool-tissue interaction forces. During minimally invasive surgeries field of view and workspace of tools are compromised due to the indirect access to the anatomy and lack of surgeon's hand-eye coordination. The sensors provide a tactile sensation to the surgeon by providing information of shape, stiffness, and texture of organ or tissue (different characteristics) to surgeon's hands through a sense of touch. This detection of a tumor through palpation, which exhibit a 'tougher' feel than healthy soft tissue, pulse felt from blood vessels, and abnormal lesions. The sensors may provide in output shape, size, pressure, softness, composition, temperature, vibration, shear, and normal forces. Sensor may be electrical or optical, consisting of capacitive, inductive, piezoelectric, piezoresistive, magnetic, and auditory. The sensors may be used in robotic, laparoscopic, palpation, biopsy, heart ablation, and valvuloplasty. Sensors can be integrated into the embodiments in a variety of manners.

Imaging systems refer to techniques or instruments which are used for the creation of images and visualization of the interior of a human body for diagnostic and treatment purposes. Imaging systems play a crucial role in every medical setting and can help in the screening of health conditions, diagnosing causes of symptoms, monitor health conditions. Imaging systems may include various imaging techniques such as X-ray, fluoroscopy, magnetic resonance imaging (MRI), ultrasound, endoscopy, elastography, tactile imaging, thermography, medical photography, and nuclear medicine e.g., positron emission tomography (PET). Some factors which may drive the market are cost and clinical advantages of medical imaging modalities, a rising share of ageing populations, increasing prevalence of cardiovascular or lifestyle diseases, increasing demand from emerging economies. Some factors which may inhibit the market are saturation in many segments, high costs, lack of trained personnel. Imaging systems can be integrated into the embodiments in a variety of manners.

X-ray refers to a medical imaging instrument that uses X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of x-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type of tissue the X-rays pass through and their densities. Some of the applications where X-rays are used may be bone fractures, infections, calcification, tumors, arthritis, blood vessel blockages, digestive problems, heart problems. The X-ray instrument may consist of components such as an x-ray tube, operating console, collimator, grids, detector, radiographic film, etc. An X-ray can be integrated into the embodiments in a variety of manners.

Magnetic resonance imaging abbreviated as MM refers to a medical imaging instrument that uses powerful magnets for the creation of images of the interior of the human body for diagnostic and treatment purposes. Some of the applications where Mill may be used may be brain/spinal cord anomalies, tumors in the body, breast cancer screening, joint injuries, uterine/pelvic pain detection, heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field, and energy release is dependent on environmental factors and the chemical nature of the molecules. MRI may more widely suit for imaging of non-bony parts or soft tissues of the body. MM may be less harmful as it does not use damaging ionizing radiation as in the X-ray instrument. MM instrument may consist of magnets, gradients, radiofrequency system, computer control system. Some areas where imaging by MRI should be prohibited may be people with implants. MM can be integrated into the embodiments in a variety of manners.

Computed tomography imaging abbreviated as CT refers to a medical imaging instrument that uses an X-ray radiation (i.e., X-ray range in the electromagnetic radiation spectrum) for the creation of cross-sectional images of the interior of the human body for diagnostic and treatment purposes. CT refers to a computerized x-ray imaging procedure in which a narrow beam of x-rays is aimed at a patient and quickly rotated around the body, producing signals that are processed by the machine's computer to generate cross-sectional images—or "slices"—of the body The CT instrument produces cross-sectional images of the body. Computed tomography instrument is different from an X-ray instrument as it creates 3-dimensional cross-sectional images of the body while X-ray creates 2-dimensional images of the body; the 3-dimensional cross-sectional images are created by taking images from different angles, which is done by taking a series of tomographic images from different angles. The different taken images are collected by a computer and digitally stacked to form a three-dimensional image of the patient. For creation of images by the CT instrument, a CT scanner uses a motorized x-ray source that rotates around the circular opening of a donut-shaped structure called a gantry while the x-ray tube rotates around the patient shooting narrow beams of x-rays through the body. Some of the applications where CT may be used may be blood clots, bone fractures, including subtle fractures not visible on X-ray, organ injuries. CT can be integrated into the embodiments in a variety of manners.

Stereotactic navigation systems refer to an instrument that uses patient imaging (e.g., CT, Mill) to guide surgeons in the placement of specialized surgical instruments and implants before and during a procedure. The patient images are taken to guide the physician before or during the medical procedure. The stereotactic navigation system includes a camera having infrared sensors to determine the location of the tip of the probe being used in the surgical procedure. This information is sent in real-time so that the surgeons have a clear image of the precise location of where they are working in the body. Stereotactic navigation systems may be framed (attachment of a frame to patient's head using screws or pins) or frameless (do not require the placement of a frame on the patient's anatomy). Stereotactic navigation systems may be used for diagnostic biopsies, tumor resection, bone preparation/implant placement, placement of electrodes, otolaryngologic, or neurosurgical procedures. Stereotactic navigation systems can be integrated into the embodiments in a variety of manners.

Ultrasound imaging also referred to as sonography or ultrasonography refers to a medical imaging instrument that uses ultrasound or sound waves (also referred to as acoustic waves) for the creation of cross-sectional images of the interior of the human body for diagnostic and treatment purposes. Ultrasound in the instrument may be produced by a piezoelectric transducer which produces sound waves and sends them into the body. The sound waves which are reflected are converted into electrical signals which are sent to an ultrasound scanner. Ultrasound instruments may be used for diagnostic and functional imaging. Ultrasound instruments may be used for therapeutic or interventional procedures. Some of the applications where ultrasound may be used are diagnosis/treatment/guidance during medical procedures e.g., biopsies, internal organs such as liver/kidneys/pancreas, fetal monitoring, etc., in soft tissues, muscles, blood vessels, tendons, joints. Ultrasound may be used for internal (transducer is placed in organs e.g., vagina) and external (transducer is placed on chest for heart monitoring or abdomen for the fetus). An ultrasound machine may consist of a monitor, keyboard, processor, data storage, probe, and transducer. Ultrasound can be integrated into the embodiments in a variety of manners.

Anesthesiology machine refers to a machine that is used to generate and mix medical gases like oxygen or air and anesthetic agents to induce and maintain anesthesia in patients. Anesthesiology machines deliver oxygen and anesthetic gas to the patient as well as filter out expiratory carbon dioxide. Anesthesia machine may perform following functions provides O2, accurately mix anesthetic gases and vapors, enable patient ventilation, and minimize anesthesia related risks to patients and staff. Anesthesia machine may consist of the following essential components a source of oxygen (O2), O2 flowmeter, vaporizer (anesthetics include isoflurane, halothane, enflurane, desflurane, sevoflurane, and methoxyflurane), patient breathing circuit (tubing, connectors, and valves), scavenging system (removes any excess anesthetics gases). Anesthesia machine may be divided into three parts the high pressure system, the intermediate pressure system, and the low-pressure system. The process of anesthesia starts with oxygen flow from pipeline or cylinder through the flowmeter, O2 flows through the vaporizer and picks up the anesthetic vapors, the O2-anesthetic mix then flows through the breathing circuit and into the patient's lungs, usually by spontaneous ventilation or normal respiration. The O2-anesthetic mix then flows through the breathing circuit and into the patient's lungs, usually by spontaneous ventilation or normal respiration. An anesthesiology machine can be integrated into the embodiments in a variety of manners.

Surgical bed is a bed equipped with mechanisms that can elevate or lower the entire bed platform, flex, or extend individual components of the platform, or raise or lower the head or the feet of the patient independently. Surgical bed may be an operation bed, cardiac bed, amputation Bed, fracture bed. Some essential components of a surgical bed may be bed sheet, woolen blanket, bath towel, bed block. Surgical beds can also be referred to as a postoperative bed, refers to a special type of bed made for the patient who is coming from the operation theatre or from another procedure that requires anesthesia. The surgical bed is designed in a manner that makes it easier to transfer an unconscious or weak patient from a stretcher/wheelchair to the bed. The surgical bed should protect bed linen from vomiting, bleeding, drainage, and discharges, provide warmth and comfort to the patient to prevent shock, provide necessary position, which is suitable for operation, protect patient from being chilled, prepared to meet any emergency. Surgical bed can be integrated into the embodiments in a variety of manners.

Disposable air warmer (also referred to as bair) refers to a convective temperature management system used in a hospital or surgery center to maintain a patient's core body temperature. The instrument consists of a reusable warming unit and a single-use disposable warming blankets for use during surgery and may also be used before and after surgery. The air warmer uses convective warming consisting of two components a warming unit and a disposable blanket. The air warmer filter air and then force warm air through disposable blankets which cover the patient. The blanket may be designed to use pressure points on the patient's body to prevent heat from reaching areas at risk for pressure sores or burns. The blanket may also include drain holes where fluid passes through the surface of the blanket to linen underneath which will reduce the risk of skin softening and reduce the risk of unintended cooling because of heat loss from evaporation. Disposable air warmer can be integrated into the embodiments in a variety of manners.

Sequential compression device abbreviated as SVD refers to an instrument that is used to help prevent blood clots in the deep veins of legs. The sequential compression device use cuffs around the legs that fill with air and squeeze your legs. This increases blood flow through the veins of your legs and helps prevent blood clots. A deep vein thrombosis (DVT) is a blood clot that forms in a vein deep inside the body. Some of the risks of using a DVT may be discomfort, warmth, or sweating beneath the cuff, skin breakdown, nerve damage, pressure injury. Sequential compression device can be integrated into the embodiments in a variety of manners.

Jackson frame refers to a frame or table which is designed for use in spine surgeries and may be used in a variety of spinal procedures in supine, prone, lateral positions in a safe manner. Two peculiar features of the Jackson table are no central table support and its ability to rotate the table through 180 degrees. The Jackson table is supported at both ends keeping the whole of the table free. This allows the visualization of trunk and major parts of extremities as well. The Jackson frame allows the patient to be slid from the cart onto the table in the supine position with appropriate padding placed. The patient is then strapped securely on the table. The Jackson frame can be integrated into the embodiments in a variety of manners.

Bed position controller refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient may be in the following positions in a bed supine position, prone position, lateral position, sims position, fowler's position, semi-Fowler's position, orthopedic or tripod position, Trendelenburg position. Bed position controller can be integrated into the embodiments in a variety of manners.

Operating room environmental controls refers to control or maintenance of the environment in an operation theatre where procedures are performed to minimize the risk of airborne infection and provide a conducive environment for everyone in the operation theatre-surgeon, anesthesiologist, nurses & patient). Some factors which may contribute to poor quality in the environment of the operating room are temperature, ventilation, and humidity and they can lead to profound effects on the health of people in the operating room and work productivity. As an example: surgeons prefer a cool, dry climate since they work in bright, hot lights; anesthesia personnel prefer a warmer, less breezy climate; patient condition demands a relatively warm, humid, and quiet environment. Operating room environmental controls may control the environment by taking care of the following factors environmental humidity, infection, odor control. Humidity control may be done by controlling the temperature of anesthesia gases; Infection can be controlled by the use of filters to purify the air. Operating room environmental controls can be integrated into the embodiments in a variety of manners.

Heating, ventilation, and air conditioning (abbreviated as HVAC) refers to a system for regulating environment of indoor settings by moving air between indoor and outdoor areas, along with heating and cooling. HVAC may use a different combination of systems, machines, and technologies to improve comfort. HVAC may be necessary to maintain the environment of an operating room. HVAC for an operating room may be a traditional operating room (which may have a large diffuser array directly above the operating table) or a hybrid operating room (which may have monitors and imaging equipment that consume valuable ceiling space and complicate the design process). HVAC may consist of three main units heating unit (it may be a furnace or a boiler), a ventilation unit (it may be natural or forced), and an air conditioning unit (which may remove existing heat). HVAC may be made of components as air return, filter, exhaust outlets, ducts, electrical elements, outdoor unit, compressor, coils, and blower. The HVAC system may use central heating and AC systems that use a single blower to circulate air via internal ducts. Heating, ventilation, and air conditioning can be integrated into the embodiments in a variety of manners.

Air purification refers to a system for removing contaminants from the air in a room to improve indoor air quality. Air purification may be important in an operating room as surgical site infection may be a reason for high mortality and morbidity. The air purification system may deliver clean, filtered, contaminant-free air over the operating room table with diffuser, airflow, etc., to remove all infectious particles down and away from the patient. Air purification system may be air curtain, multi-diffuser array, or single large diffuser (based on laminar diffuser flow) or high-efficiency particulate air filter. high-efficiency particulate air filter referred to as HEPA filter protects from infection and contamination by a filter which is mounted at the terminal of the duct. HEPA filter may be mounted on the ceiling and deliver clean, filtered air in a flow to the room that provides a sweeping effect that pushes contaminants out via the return grilles that are usually mounted on the lower wall. Air purification can be integrated into the embodiments in a variety of manners.

Orthopedic tools also referred to as orthopedic instruments used for treatment and prevention of deformities and injuries of musculoskeletal system or skeleton, articulations, and locomotive system (i.e., set formed by skeleton, muscles attached to it and part of nervous system which controls the muscles). Major percentage of orthopedic tools are made of plastic. Orthopedic tools may be divided into the following specialties hand and wrist, foot and ankle, shoulder and elbow, arthroscopy, hip, and knee. Orthopedic tool may be fixation tools, relieving tools, corrective tools, compression-distraction tools. Fixation tool refers to a tool designed to restrict movements partially or completely in a joint, e.g., hinged splints (for preserving a certain range of movement in a joint), rigid splints. Relieving tool refers to a tool designed to relieve pressure on an ailing part by transferring support to healthy parts of an extremity, e.g., Thomas splint and the Voskoboinikova apparatus. Corrective tool refers to a tool designed to gradually correct a deformity, e.g., corsets, splints, orthopedic footwear, and insoles and other devices to correct abnormal positions of the foot. Compression-distraction tool refers to a tool designed to correct acquired or congenital deformities of the extremities, e.g., curvature, shortening, and pseudarthrosis such as Gudushauri. Fixation tools may be internal fixation tools (e.g., screws, plates) or external fixation tools (radius, tibia fracture fixation). Orthopedic tools may be bone-holding forceps, drill bits, nail pins, hammer staple, etc. Orthopedic tools can be integrated into the embodiments in a variety of manners.

Drill refers to a tool for making holes in bones for insertion of implants like nails, plates, screws, and wires. The drill tool functions by drilling cylindrical tunnels into bone. Drill may be used in orthopedics for performing medical procedures. Use of drill on bones may have some risks harm caused to bone, muscle, nerves, and venous tissues are wrapped by surrounding tissue, the drill does not stop immediately. Drills vary widely in speed, power, and size. Drill may be powered as electrical, pneumatic, or battery. Drills generally may work on speed below 1000 rpm in orthopedic. Temperature control of drill is an important aspect in the functioning of drill and is dependent on parameters rotation speed, torque, orthotropic site, sharpness of the cutting edges, irrigation, cooling systems. The drill may consist of components physical drill, cord power, electronically motorized bone drill, rotating bone shearing incision work unit. Drill can be integrated into the embodiments in a variety of manners.

Scalpel refers to a tool for slicing or cutting or osteotomy of bone during orthopedic procedure. The scalpel may be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate and performs cutting by an ultrasonically oscillating or forward/backward moving metal tip. Scalpel may prevent injuries caused by a drill in a spinal surgery such as complications such as nerve thermal injury, grasping soft tissue, tearing dura mater, and a mechanical injury may occur during drilling. Scalpel can be integrated into the embodiments in a variety of manners.

Stitches (also referred to as sutures) refers to a sterile, surgical thread used to repair cuts or lacerations and are used to close incisions or hold body tissues together after a surgery or an injury. Stitches may involve the use of a needle along with an attached thread. Stitches may be of type absorbable (the stitches automatically break down harmlessly in the body over time without intervention) and non-absorbable (the stitches do not automatically break down over time and must be manually removed if not left indefinitely). Stitches may be of type based on material monofilament, multifilament, and barb. Stitches may be classified based on size. Stitches may be of type based on material synthetic and natural. Stitches may be of type based on coating coated and un-coated. Stitches can be integrated into the embodiments in a variety of manners.

Stapler refers to a tool for fragment fixation when interfragmental screw fixation is not easy. When there is vast damage and bone is broken into fragments then staples can be used between these fragments for internal fixation and bone reconstruction. For example, they may be used around joints as in ankle and foot surgeries, in cases of soft tissue damage, to attach tendons or ligaments to the bone for reconstruction surgery. Stapler may be made of surgical grade stainless steel or titanium, and they are thicker, stronger, and larger. The stapler can be integrated into the embodiments in a variety of manners.

Equipment refers to a set of articles, tools, or objects which help to implement or achieve an operation or activity. A medical equipment refers to an article, instrument, apparatus, or machine used for diagnosis, prevention, or treatment of a medical condition or disease or detection, measurement, restoration, correction, or modification of structure/function of the body for some health purpose. The medical equipment may perform functions invasively or non-invasively. The medical equipment may consist of components sensor/transducer, signal conditioner, display, data storage unit, etc. The medical equipment works by taking a signal from a measurand/patient, a transducer for converting one form of energy to electrical energy, signal conditioner such as an amplifier, filters, etc., to convert the output from the transducer into an electrical value, display to provide a visual representation of measured parameter or quantity, a storage system to store data which can be used for future reference. A medical equipment may perform any function of diagnosis or provide therapy, for example, the equipment delivers air/breaths into the lungs and moves it out of the lungs and out of lungs, to a patient who is physically unable to breathe, or breaths insufficiently. A medical equipment can be integrated into the embodiments in a variety of manners.

Ventilator (also referred to as a respirator) refers to an instrument that provides a patient with oxygen when they are unable to breathe on their own. The ventilator is required when a person is not able to breathe on their own. The ventilator may perform a function of pushing air into the lungs and allows it to come back out, gently like lungs when they are working. Ventilator functions by delivery of positive pressure to force air into your lungs, while usual breathing uses negative pressure by the opening of the mouth, and air flows in. The machine uses positive pressure to force air into your lungs. A ventilator may be required during surgery or after surgery. A ventilator may be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator may be used with a face mask (non-invasive ventilation, where the ventilation is required for a shorter duration of time) or with a breathing tube also referred to as an endotracheal tube (invasive ventilation, where the ventilation is required for a longer duration of time). A ventilator use may have some risks such as infections, fluid build-up, muscle weakness, lung damage, etc. A ventilator may be operated in modes ACV, SIMV, PCV, PSV, PCIRV, APRV, etc. A ventilator may have components gas delivery system, power source, control system, safety feature, gas filter, monitor. A ventilator can be integrated into the embodiments in a variety of manners.

Continuous positive airway pressure abbreviated as CPAP refers to an instrument which used for the treatment of sleep apnea disorder in a patient. Sleep apnea refers to a disorder in which breathing repeatedly stops and starts while a patient is sleeping, often because throat/airways briefly collapse or something temporarily blocks them and may lead to serious health problems, such as high blood pressure and heart trouble. Continuous positive airway pressure instrument helps the patient with sleep apnea to breathe more easily during sleep by sending a steady flow of oxygen into the nose and mouth during sleep, which keeps the airways open and helps to breathe normally. The CPAP machine may work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP may have a nasal pillow mask, nasal mask, or full mask. CPAP instrument may consist of components a motor, a cushioned mask, a tube that connects the motor to the mask, a headgear frame, adjustable straps. The essential components may be a motor, a cushioned mask, a tube that connects the motor to the mask. Continuous positive airway pressure instruments can be integrated into the embodiments in a variety of manners.

Consumables refer to necessary supplies for health systems to provide care within a hospital or surgical environment. Consumables may include gloves, gowns, masks, syringes, needles, sutures, staples, tubing, catheters, and adhesives for wound dressing, in addition to other tools needed by doctors and nurses to provide care. Depending on the device mechanical testing may be carried out in tensile, compression or flexure, in dynamic or fatigue, or impact or with the application of torsion. Consumables may be disposable (are timesaving, no risk of healthcare-associated infections, cost-efficient) or sterilizable (cross-contamination, risk of surgical site infections, sterilization). Consumables can be integrated into the embodiments in a variety of manners.

Robotic systems refer to systems that provide intelligent services and information by interacting with their environment, including human beings, via the use of various sensors, actuators, and human interfaces. These are employed for automating processes in a wide range of applications, ranging from industrial (manufacturing), domestic, medical, service, military, entertainment, space, etc. The adoption of robotic systems provides several benefits, including efficiency and speed improvements, lower costs, and higher accuracy. Performing medical procedures with the assistance of robotic technology are referred to as medical robotic systems. The medical robotic system market can be segmented by product type into surgical robotic systems, rehabilitative robotic systems, non-invasive radiosurgery robots, hospital & pharmacy robotic systems. Robotic technologies have offered valuable enhancements to medical or surgical processes through improved precision, stability, and dexterity. Robots in medicine help by relieving medical personnel from routine tasks, and by making medical procedures safer and less costly for patients. They can also perform accurate surgery in tiny places and transport dangerous substances. Robotic surgeries are performed using tele-manipulators, which use the surgeon's actions on one side to control the "effector" on the other side. A medical robotic system ensures precision and may be used for remotely controlled, minimally invasive procedures. The systems comprise computer-controlled electromechanical devices that work in response to controls manipulated by the surgeons. Robotic systems can be integrated into the embodiments in a variety of manners.

An electronic health record (EHR) refers to a digital record of a patient's health information, which may be collected and stored systematically over time. It is an all-inclusive patient record and could include demographics, medical history, history of present illness (HPI), progress notes, problems, medications, vital signs, immunizations, laboratory data, and radiology reports. A computer software is used to capture, store, and share patient data in a structured way. The EHR may be created and managed by authorized providers and can make health information instantly accessible to authorized providers across practices and health organizations—such as laboratories, specialists, medical imaging facilities, pharmacies, emergency facilities, etc. The timely availability of EHR data can enable healthcare providers to make more accurate decisions and provide better care to the patients by effective diagnosis and reduced medical errors. Besides providing opportunities to enhance patient care, it may also be used to facilitate clinical research by combining all patients' demographics into a large pool. For example, the EHR data can support a wide range of epidemiological research on the natural history of disease, drug utilization, and safety, as well as health services research. The EHR can be integrated into the embodiments in a variety of manners.

Equipment tracking systems, such as RFID, refers to a system that tags an instrument with an electronic tag and tracks it using the tag. Typically, this could involve a centralized platform that provides details such as location, owner, contract, and maintenance history for all equipment in real-time. A variety of techniques can be used to track physical assets, including radio-frequency identification (RFID), global positioning system (GPS), Bluetooth low energy (BLE), barcodes, near-field communication (NFC), Wi-Fi, etc. The equipment tracking system comprises the hardware components, such as RFID tags, GPS trackers, barcodes, and QR codes. The hardware component is placed on the asset, and it communicates with the software (directly or via a scanner), providing it with data about the asset's location and properties. An equipment tracking system uses electromagnetic fields to transmit data from an RFID tag to a reader. Reading of RFID tags may be done by portable or mounted RFID readers. RFID may be very short for low frequency or high frequency for ultra-high frequency. Managing and locating important assets is a key challenge for tracking medical equipment. Time spent searching for critical equipment can lead to expensive delays or downtime, missed deadlines and customer commitments, and wasted labor. The problem has been solved by the use of barcode labels or using manual serial numbers and spreadsheets; however, these require manual labor. The RFID tag may be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own). Equipment tracking systems may offer advantages, no line of sight required, read Multiple RFID objects at once, scan at a distance, and flexibility. Equipment tracking systems, RFID can be integrated into the embodiments in a variety of manners.

Quantum computing refers to any computational device or method which utilizes properties of quantum states defined by quantum mechanics such as superposition, entanglement, etc. to perform computations. These devices utilize qubits which are the quantum equivalent to bits in a classical computing system, comprised of at least two quantum states or probable outcomes. These outcomes, combined with a coefficient representing the probability of each outcome, describes the possible states, or bits of data, which can be represented by the qubits according to the principle of quantum superposition. These states may be manipulated which may shift the probability of each outcome or additionally add additional possible outcomes to perform a calculation, the final state of which can be measured to achieve the result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that nature of quantum computing is the same as the systems being simulated. In medical fields, quantum computing shows the greatest promise for drug discovery and simulating the interaction of drugs with biologic systems, however the same technology might be used to predict the interaction of a biologic system with an implanted device, preventing rejection of an implant by a patient's body, long term function of an implant, and potentially the reaction of a patient to a surgical procedure during a simulation before a procedure or actively during a procedure.

Figure 11:
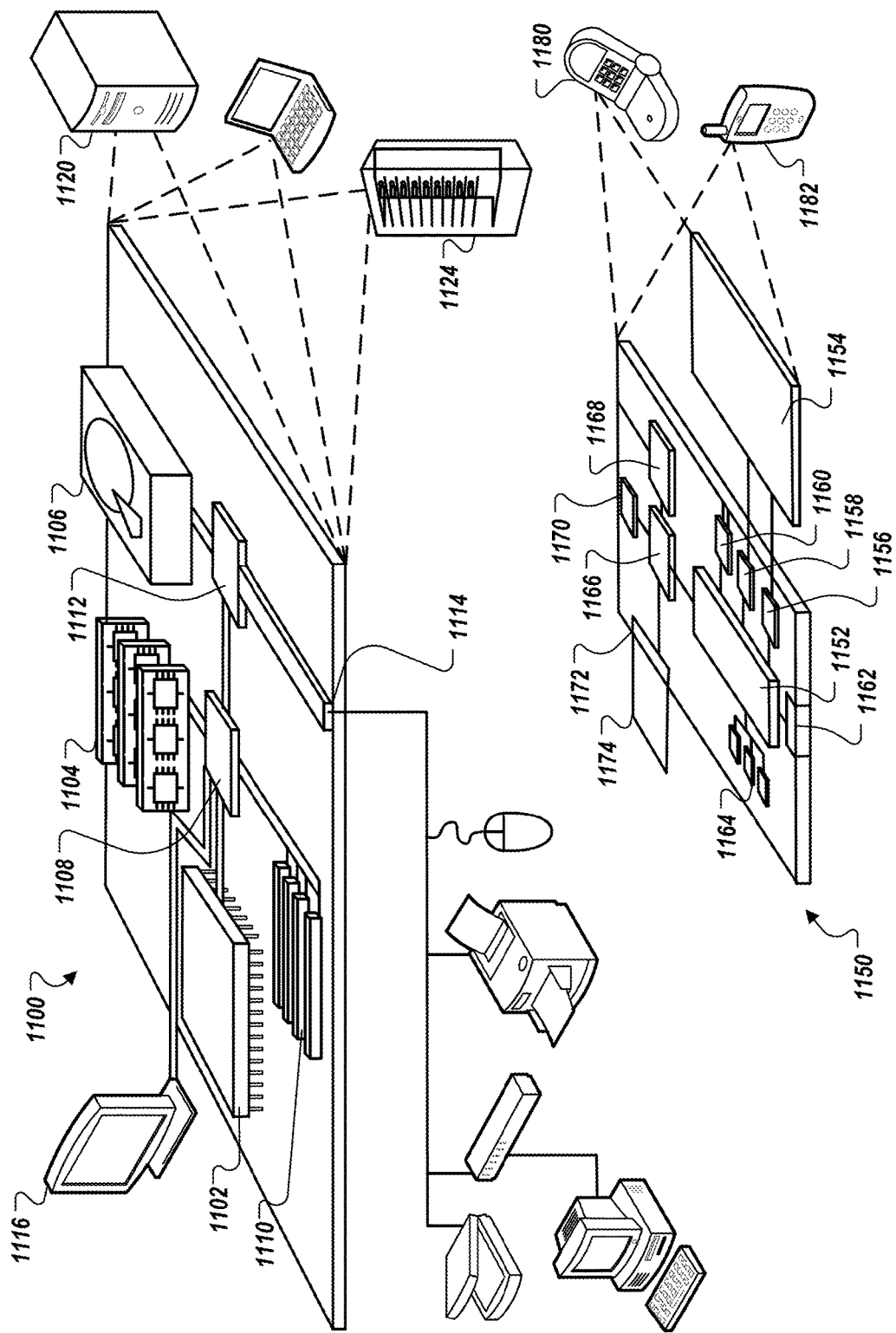
FIG. 11 is a schematic diagram that shows an example of a computing device and a mobile computing device.

FIG. 11 shows an example of a computing device 1100 and an example of a mobile computing device that can be used to implement the techniques described here. The computing device 1100 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1100 includes a processor 1102, a memory 1104, a storage device 1106, a high-speed interface 1108 connecting to the memory 1104 and multiple high-speed expansion ports 1110, and a low-speed interface 1112 connecting to a low-speed expansion port 1114 and the storage device 1106. Each of the processor 1102, the memory 1104, the storage device 1106, the high-speed interface 1108, the high-speed expansion ports 1110, and the low-speed interface 1112, are interconnected using various busses, and can be mounted on a common motherboard or in other manners as appropriate. The processor 1102 can process instructions for execution within the computing device 1100, including instructions stored in the memory 1104 or on the storage device 1106 to display graphical information for a GUI on an external input/output device, such as a display 1116 coupled to the high-speed interface 1108. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 1104 stores information within the computing device 1100. In some implementations, the memory 1104 is a volatile memory unit or units. In some implementations, the memory 1104 is a non-volatile memory unit or units. The memory 1104 can also be another form of computer-readable medium, such as a magnetic or optical disk.

The storage device 1106 is capable of providing mass storage for the computing device 1100. In some implementations, the storage device 1106 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1104, the storage device 1106, or memory on the processor 1102.

The high-speed interface 1108 manages bandwidth-intensive operations for the computing device 1100, while the low-speed interface 1112 manages lower bandwidth-intensive operations. Such allocation of functions is exemplary only. In some implementations, the high-speed interface 1108 is coupled to the memory 1104, the display 1116 (e.g., through a graphics processor or accelerator), and to the high-speed expansion ports 1110, which can accept various expansion cards (not shown). In the implementation, the low-speed interface 1112 is coupled to the storage device 1106 and the low-speed expansion port 1114. The low-speed expansion port 1114, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 1100 can be implemented in a number of different forms, as shown in the figure. For example, it can be implemented as a standard server 1120, or multiple times in a group of such servers. In addition, it can be implemented in a personal computer such as a laptop computer 1122. It can also be implemented as part of a rack server system 1124. Alternatively, components from the computing device 1100 can be combined with other components in a mobile device (not shown), such as a mobile computing device 1150. Each of such devices can contain one or more of the computing device 1100 and the mobile computing device 1150, and an entire system can be made up of multiple computing devices communicating with each other.

The mobile computing device 1150 includes a processor 1152, a memory 1164, an input/output device such as a display 1154, a communication interface 1166, and a transceiver 1168, among other components. The mobile computing device 1150 can also be provided with a storage device, such as a micro-drive or other device, to provide additional storage. Each of the processor 1152, the memory 1164, the display 1154, the communication interface 1166, and the transceiver 1168, are interconnected using various buses, and several of the components can be mounted on a common motherboard or in other manners as appropriate.

The processor 1152 can execute instructions within the mobile computing device 1150, including instructions stored in the memory 1164. The processor 1152 can be implemented as a chipset of chips that include separate and multiple analog and digital processors. The processor 1152 can provide, for example, for coordination of the other components of the mobile computing device 1150, such as control of user interfaces, applications run by the mobile computing device 1150, and wireless communication by the mobile computing device 1150.

The processor 1152 can communicate with a user through a control interface 1158 and a display interface 1156 coupled to the display 1154. The display 1154 can be, for example, a TFT (Thin-Film-Transistor Liquid Crystal Display) display or an OLED (Organic Light Emitting Diode) display, or other appropriate display technology. The display interface 1156 can comprise appropriate circuitry for driving the display 1154 to present graphical and other information to a user. The control interface 1158 can receive commands from a user and convert them for submission to the processor 1152. In addition, an external interface 1162 can provide communication with the processor 1152, so as to enable near area communication of the mobile computing device 1150 with other devices. The external interface 1162 can provide, for example, for wired communication in some implementations, or for wireless communication in other implementations, and multiple interfaces can also be used.

The memory 1164 stores information within the mobile computing device 1150. The memory 1164 can be implemented as one or more of a computer-readable medium or media, a volatile memory unit or units, or a non-volatile memory unit or units. An expansion memory 1174 can also be provided and connected to the mobile computing device 1150 through an expansion interface 1172, which can include, for example, a SIMM (Single In Line Memory Module) card interface. The expansion memory 1174 can provide extra storage space for the mobile computing device 1150, or can also store applications or other information for the mobile computing device 1150. Specifically, the expansion memory 1174 can include instructions to carry out or supplement the processes described above, and can include secure information also. Thus, for example, the expansion memory 1174 can be provide as a security module for the mobile computing device 1150, and can be programmed with instructions that permit secure use of the mobile computing device 1150. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1164, the expansion memory 1174, or memory on the processor 1152. In some implementations, the computer program product can be received in a propagated signal, for example, over the transceiver 1168 or the external interface 1162.

The mobile computing device 1150 can communicate wirelessly through the communication interface 1166, which can include digital signal processing circuitry where necessary. The communication interface 1166 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1168 using a radio-frequency. In addition, short-range communication can occur, such as using a Bluetooth, WiFi, or other such transceiver (not shown). In addition, a GPS (Global Positioning System) receiver module 1170 can provide additional navigation- and location-related wireless data to the mobile computing device 1150, which can be used as appropriate by applications running on the mobile computing device 1150.

The mobile computing device 1150 can also communicate audibly using an audio codec 1160, which can receive spoken information from a user and convert it to usable digital information. The audio codec 1160 can likewise generate audible sound for a user, such as through a speaker, e.g., in a handset of the mobile computing device 1150. Such sound can include sound from voice telephone calls, can include recorded sound (e.g., voice messages, music files, etc.) and can also include sound generated by applications operating on the mobile computing device 1150.

The mobile computing device 1150 can be implemented in a number of different forms, as shown in the figure. For example, it can be implemented as a cellular telephone 1180. It can also be implemented as part of a smart-phone 1182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A method for designing 3D printed objects for insertion into a body of a patient, the method comprising;
   receiving, from a medical imaging device, image data of at least a portion of a patient's body;
   generating, based on the image data, a 3D representation of the portion of the patient's body;
   retrieving, from a database, historic patient data for other patients that have a same or similar health condition as the patient;
   generating at least one recommendation for a design of a 3D printed object to be inserted into the portion of the patient's body based on a comparison of the 3D representation of the portion of the patient's body to the retrieved historic patient data,
   wherein generating the at least one recommendation for the design of the 3D printed object to be inserted into the portion of the patient's body comprises scoring a result from the comparison of the 3D representation of the portion of the patient's body to the retrieved historic patient data, wherein a score value for the result is determined based on whether a size of the 3D printed object would fit within spatial limits of the portion of the patient's body, and wherein the score value is assigned above a threshold score value based on a determination that the size of the 3D printed object is within a threshold size range as the portion of the patient's body;

transmitting instructions to a user computing device that, when executed using one or more processors, cause the user computing device to output in a graphical user interface (GUI) display the 3D printed object and the at least one recommendation;

receiving, from the user computing device, an altered 3D representation of the portion of the patient's body, wherein a user at the user computing device provided user input, using one or more tools displayed in the GUI display, to alter the 3D representation based on the at least one recommendation;

running a simulation to test the design of the 3D printed object based on the altered 3D representation of the portion of the patient's body; and returning simulation results based on running the simulation.

2. The method of claim 1, wherein returning the simulation results includes: in response to a successful simulation result, executing instructions that cause a printing device to print the design of the 3D printed object according to the altered 3D representation.

3. The method of claim 2, wherein the printing device is a 3D printer.

4. The method of claim 2, further comprising: in response to printing the design of the 3D printed object, running another simulation to test compatibility of the printed object and a physiology of the patient.

5. The method of claim 4, further comprising: in response to a successful simulation result from testing the compatibility of the printed object and the physiology of the patient, transmitting a notification to the user computing device indicating that the printed object is compatible with the physiology of the patient and is ready to be inserted into the patient's body.

6. The method of claim 1, wherein returning the simulation results includes: in response to an unsuccessful simulation result, generating one or more other recommendations to modify the design of the 3D printed object.

7. The method of claim 6, further comprising: iteratively modifying the design of the 3D printed object based on (i) user input indicating one or more modifications to the design of the 3D printed object based on the other recommendations and (ii) running one or more other simulations to test the modified design of the 3D printed object.

8. The method of claim 1, wherein the 3D representation of the portion of the patient's body comprises an area of concern in the patient's body where the 3D printed object is to be inserted.

9. The method of claim 1, wherein the 3D printed object is at least one of an implant, a stent, an apparatus, an anatomical structure, and an organ.

10. The method of claim 1, wherein the score value for the result is assigned a highest score value based on a determination that the size of the 3D printed object would fit exactly within the spatial limits of the portion of the patient's body.

11. The method of claim 1, wherein running the simulation comprises determining a success rate of printing the 3D printed object according to the design.

12. The method of claim 1, wherein running the simulation comprises determining a success rate of inserting the 3D printed object into the portion of the patient's body.

13. The method of claim 1, wherein running the simulation comprises determining whether the 3D printed object would interact with anatomical structures inside the patient's body near the portion of the patient's body where the 3D printed object is inserted.

14. The method of claim 1, wherein running the simulation comprises determining whether measurements of the 3D printed object are within a threshold range of measurements of an object in the portion of the patient's body that is to be replaced by the 3D printed object.

15. The method of claim 1, wherein running the simulation comprises determining a likelihood that the 3D printed object, once inserted into the portion of the patient's body, would fail or cause future health conditions for the patient.

16. A system for designing 3D printed objects for insertion into a body of a patient, the system comprising:

at least one imaging device configured to capture image data of at least a portion of a patient's body;

a user computing device having a graphical user interface (GUI) display, wherein the user computing device is configured to receive and output information for designing an object to be 3D printed and inserted into the portion of the patient's body;

a printing device configured to print the object; and a computing system in communication with the at least one imaging device, the user computing device, and the printing device, wherein the computing system is configured to perform operations comprising:

receiving, from the at least one imaging device, image data of at least a portion of the patient's body;

generating, based on the image data, a 3D representation of the portion of the patient's body;

retrieving, from a database, historic patient data for other patients that have a same or similar health condition as the patient;

generating at least one recommendation for a design of a 3D printed object to be inserted into the portion of the patient's body based on a comparison of the 3D representation of the portion of the patient's body to the retrieved historic patient data, wherein generating the at least one recommendation for the design of the 3D printed object to be inserted into the portion of the patient's body comprises scoring a result from the comparison of the 3D representation of the portion of the patient's body to the retrieved historic patient data, wherein a score value for the result is determined based on whether a size of the 3D printed object would fit within spatial limits of the portion of the patient's body, and wherein the score value is assigned above a threshold score value based on a determination that the size of the 3D printed object is within a threshold size range as the portion of the patient's body;

transmitting instructions to the user computing device that, when executed using one or more processors, cause the user computing device to output in a graphical user interface (GUI) display the 3D printed object and the at least one recommendation;

receiving, from the user computing device, an altered 3D representation of the portion of the patient's body, wherein a user at the user computing device provided user input, using one or more tools displayed in the GUI display, to alter the 3D representation based on the at least one recommendation;

running a simulation to test the design of the 3D printed object based on the altered 3D representation of the portion of the patient's body; and returning simulation results based on running the simulation.

17. The system of claim 16, wherein the computing system comprises:

an imaging module configured to control operation of the at least one imaging device and generate the 3D representation of the portion of the patient's body;

a design module configured to receive, from the user computing device, the altered 3D representation of the portion of the patient's body;

an enhancement module configured to generate the at least one recommendation for the design of the 3D printed object;

a simulation module configured to run the simulation module; and a print module configured to control operation of the printing device.

* * * * *

UNITED STATES PATENT AND TRADEMARK OFFICE
CERTIFICATE OF CORRECTION

PATENT NO. : 11,963,724 B1  
APPLICATION NO. : 18/216209  
DATED : April 23, 2024  
INVENTOR(S) : Jeffrey Roh et al.

Page 1 of 1

It is certified that error appears in the above-identified patent and that said Letters Patent is hereby corrected as shown below:

On the Title Page

Item (73), delete "1X" and insert -- IX --.

Signed and Sealed this
Twentieth Day of August, 2024

Katherine Kelly Vidal
*Director of the United States Patent and Trademark Office*